(12) United States Patent
Li et al.

(10) Patent No.: US 10,266,489 B2
(45) Date of Patent: Apr. 23, 2019

(54) PYRROLIC AMIDE COMPOUND AND PREPARATION METHOD AND APPLICATION THEREOF

(71) Applicant: HitGen LTD, Chengdu (CN)

(72) Inventors: Jin Li, Chengdu (CN); Dengfeng Dou, Chengdu (CN); Jinqiao Wan, Chengdu (CN); Fei Pan, Chengdu (CN); Peng Lv, Chengdu (CN)

(73) Assignee: HitGen LTD, Chengdu (CN)

( * ) Notice: Subject to any disclaimer, the term of this patent is extended or adjusted under 35 U.S.C. 154(b) by 0 days.

(21) Appl. No.: 15/635,181

(22) Filed: Jun. 27, 2017

(65) Prior Publication Data

US 2017/0298016 A1 Oct. 19, 2017

Related U.S. Application Data

(63) Continuation of application No. PCT/CN2015/090291, filed on Sep. 22, 2015.

(30) Foreign Application Priority Data

Dec. 29, 2014 (CN) .......................... 2014 1 0836191

(51) Int. Cl.
  *C07D 207/48* (2006.01)
  *A61K 31/40* (2006.01)
  *C07D 401/12* (2006.01)
  *C07D 405/12* (2006.01)

(52) U.S. Cl.
  CPC ............ *C07D 207/48* (2013.01); *A61K 31/40* (2013.01); *C07D 401/12* (2013.01); *C07D 405/12* (2013.01)

(58) Field of Classification Search
  CPC ... C07D 207/48; C07D 401/12; C07D 405/12
  See application file for complete search history.

(56) References Cited

FOREIGN PATENT DOCUMENTS

| CN | 102659630 A | 9/2012 |
|---|---|---|
| CN | 102786458 A | 11/2012 |
| CN | 103288728 A | 9/2013 |
| CN | 103420917 A | 12/2013 |
| CN | 103467359 A | 12/2013 |
| CN | 103539695 A | 1/2014 |
| WO | 2005068448 A1 | 7/2005 |
| WO | 2005113542 A2 | 12/2005 |
| WO | 2010014054 A1 | 2/2010 |

OTHER PUBLICATIONS

Vippagunta, et al. Advanced Drug Delivery Reviews 48 (2001) 3-26.*
Concise Encyclopedia Chemistry (1993) Walter de Gruyter Berlin New York.*

* cited by examiner

*Primary Examiner* — Shawquia Jackson
(74) *Attorney, Agent, or Firm* — Wayne & Ken, LLC; Tony Hom

(57) ABSTRACT

The present invention discloses a pyrrolic amide compound shown as a formula I, or crystal forms thereof, and pharmaceutically acceptable salts, hydrates or solvates, wherein $R_1$ is selected from hydrogen, hydroxyl, cyano, halogen, carboxyl, $C_1$-$C_6$ alkyl and the like; $R_2$ is selected from hydrogen, hydroxyl, cyano, halogen and the like; $R_3$ is selected from hydroxyl and the like; X is selected from

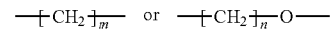

group, m is equal to 0, 1, 2 or 3, and n is equal to 0, 1 or 2. The novel compound shown as the formular I provided by the present invention has high deacetylase inhibitory viability; and meanwhile, a method for preparing the novel compound in the present invention has the advantages of fewer steps, simple and convenient operation, safety, environment friendliness, high yield and the like and is very suitable for industrial application.

Formula I

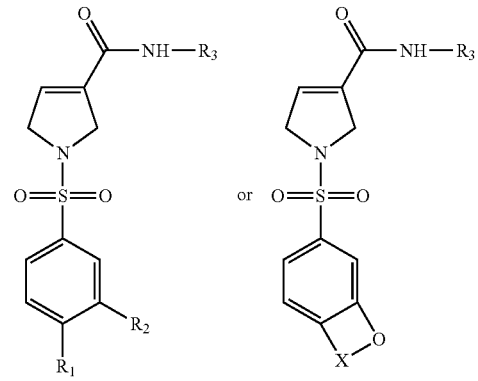

5 Claims, No Drawings

PYRROLIC AMIDE COMPOUND AND PREPARATION METHOD AND APPLICATION THEREOF

TECHNICAL HELD

The present invention relates to a pyrrolic amide compound and a preparation method and an application thereof, and particularly relates to a pyrrolic amide compound with histone deacetylase inhibitory viability and a preparation method and an application thereof.

BACKGROUND

Inactivation of genes for controlling cell growth in organisms is a tumorigenesis marker. Epigenetic mechanisms causing gene inactivation mainly include DNA methylation, histone acetylation and modifications of other ingredients in higher-order chromatin structures. These modifications change chromatin configurations to cause achange of gene transcription regulation. Genetic transcription disorders may cause abnormal cell proliferation, thereby causing tumors.

More than 40 years ago, Allfrey et al. has recognized that the histone acetylation process is closely related to eukaryotic gene transcriptional regulation (Allfrey V G, Faulkner R, Mirsky A E. Acetylation and methylation of histones and their possible role in the regulation of RNA synthesis [J]. Proc Natl Acad Sci USA, 1964, 51: 786-794). The historic acetylation plays a key role in transcriptional regulation of eukaryocytes. The acetylation modification of histone occurs on an epsilon-amino of N-terminal evolutionarily conserved lysine residues and the modification on H3 and H4 is more universal than that on H2A and H2B. Relatively important acetylation loci refer to $Lys^9$ and $Lys^{14}$ on H3 and $Lys^5$, $Lys^8$, $Lys^{12}$ and $Lys^{16}$ on H4. Through acetylation of HAT, aminos of N-terminal lysine of histone are acetylated, positive charges on the aminos are eliminated, negative charges on DNA molecules contribute to spreading DNA conformation, nucleosome structures are relaxed, transcription factors and collaborative transcription activators are facilitated to contact with the DNA molecules, and the histone acetylation can activate specific gene transcriptional expression. Conversely, the histone acetylation is not favorable for expressions of specific genes (such as Rb, p21 and p27). The acetylation and deacetylation of the histone become selector switches of the expressions of the specific genes (Thiagalingam S, Cheng K H, Lee H J, et al. Histonedeacetylases: unique players in shaping the epigenetic histone code [J]. Ann N Y Acad. Sci, 2003, 983; 84-100).

The histone acetylation is regulated by a pair of proteases with mutually antagonistic functions, that is, histone acetyltransferases (HATs) and histone deacetylases (HDACs). The pair of proteases is in a dynamic balance state in normal cells. Generally, histone acetylation level enhancement is related to gene transcription viability enhancement, while too low acetylation level is related to gene expression inhibition (Forsberg E C, Bresnick E H. Histone acetylation beyond promoters: long-range acetylation patterns in the chromatin world[J]. Bioessays, 2001, 23(9): 820-830). Research finds that the HDAC is overexpressed and recruited by a transcription factor to cause abnormal inhibition of the specific genes, thereby causing tumors and other diseases; however, the HDAC viability inhibition may cause growth inhibition and apoptosis of many cancer cells (Somech R, Izraeli S, J Simon A. Histone deacetylase inhibitors-a new tool to treat cancer [J]. Cancer Treat Rev, 2004, 30(5): 461-472). Therefore, the HDAC has become a latest and most popular target in the existing anti-tumor drug research and development field.

An HDAC inhibitor can inhibit HDAC enzyme viability, and an action mechanism of the inhibitor is to block inhibited gene expression caused by HDAC recruiting dysfunctions by inhibiting the HDAC and to change a chromatin structure by changing the degree of acetylation of the histone, thereby regulating the gene expression to treat cancers. The inhibitor has obvious curative effects for treating hematopoietic tumors and solid tumors by inducing growth arrest, differentiation or apoptosis of tumor cells. The HDAC inhibitor has tumor specificity and has a cytotoxic effect to proliferative and dormant aberrant cells, while normal cells have more than 10 times of tolerance to the HDAC inhibitor, and growth arrest and apoptosis of the normal cells may not be caused. Moreover, the clinical dosage of the HDAC inhibitor is far lower than the maximum human tolerance, and the inhibitor has low toxicity to the organisms. The development and utilization of the HDAC inhibitor has become a new hot spot of tumor therapy.

At present, the HDAC inhibitors which have been researched and developed can he classified into five categories: (1) hydroxamic acid compounds with a functional group of hydroximic acid, including representatives such as TSA, SAHA (Curtin M L, Garland R B, Heyman H R, et al. Succinimide hydroxamic acids as potent inhibitors of histone deacetylase[J]. Bioorg Med Chem Lett, 2002, 12(20) 2919-2923), LAQ824 (Atadja P, Hsu M, Kwon P, et al. Moleculer and cellular basis for the anti-proliferative effects of the HDAC inhibitor LAQ824. Novartis Found Symp, 2004, 259: 249-266); (2) cyclic tetrapeptides containing 2-amino-8-oxo-9,10-epoxy capryl or not containing the group, such as FK-228; (3) benzamide compounds, wherein a representative MS-275 has been clinically studied; (4) short-chain fatty acids, such as butyric acid and phenylbutyric acid; and (5) others; the HDAC inhibitors do not have structural characteristics of general HDAC, but contain some or all structural subunits required for inhibiting the HDAC viability.

For example, a Chinese patent CN 103420917 A discloses a benzamide compound containing a condensed ring structure shown as a formula A, and histone deacetylase inhibitory viability and applications in treating malignant tumors and differentiation and proliferation related diseases. A Chinese patent CN 103288728 A discloses a naphthoamide derivative shown as a formul B, and the naphthoamide derivative can effectively treat some diseases caused by protein kinase regulation abnormality. A Chinese patent CN 103539695 A discloses a substituted diphenyl ether histone deacetylase inhibitor shown as a formula C. A Chinese patent CN 103467359 A discloses an indole-containing cinnamamide histone deacetylase inhibitor shown as a formula D. A Chinese patent. CN 102659630 A discloses a hydroxamic acid compound shown as a formula E.

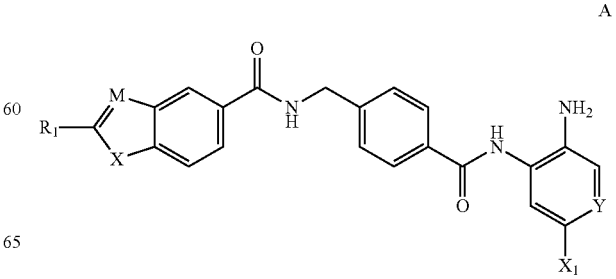

A

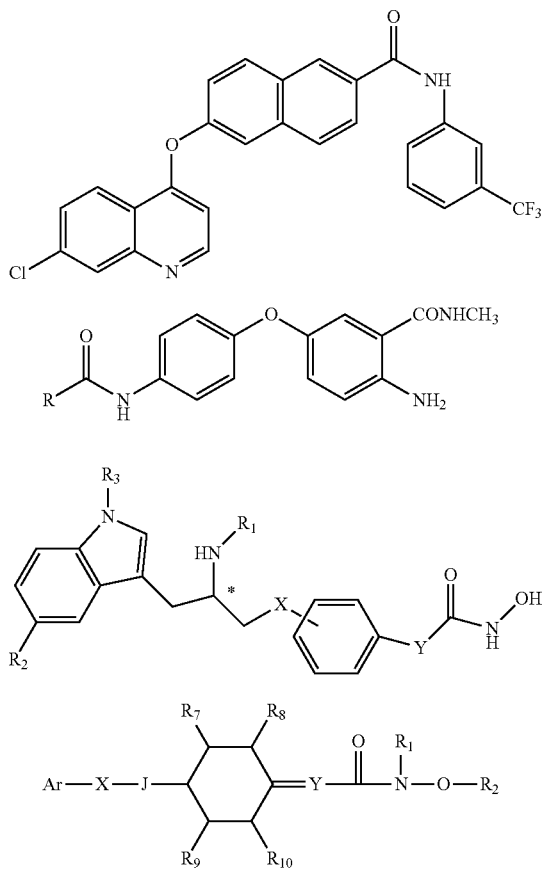

A Chinese patent CN 102786458 A discloses a pyrrole formamide derivative shown as a formula F, application as an anti-malignant tumor drug, and particularly an application in preparing medicines for treating breast cancer, lung cancer and gastric cancer.

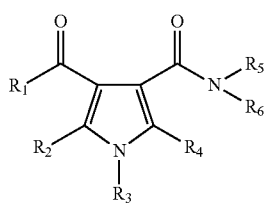

$R_1$, $R_2$, $R_3$ and $R_4$ are: $C_1$-$C_6$ linear alkyl or branched alkyl, $C_3$-$C_6$ naphthenic base;

$R_5$ and $R_6$ are simultaneously or respectively: hydrogen $C_1$-$C_6$ alkyl; hydroxyl, halogen, $C_1$-$C_4$ alkoxy, nitrate-substituted $C_1$-$C_6$ alkyl.

At present, SAHA developed by Merck company is a listed histone deacetylase inhibitor, is only limited to treatment of skin T cell lymphoma and does not have obvious curative effects on many other cancers. Other developed HDAC inhibitors have certain problems in antitumor viability, toxic and side effects, subtype selectivity and the like. Therefore, development of a novel compound with the histone deacetylase inhibitory viability has very important social and economic significances.

SUMMARY

The present invention aims to provide a pyrrolic amide compound.

The present invention provides a pyrrolic amide compound shown as a formula I, or crystal forms thereof, and pharmaceutically acceptable salts, hydrates or solvates:

Formula I

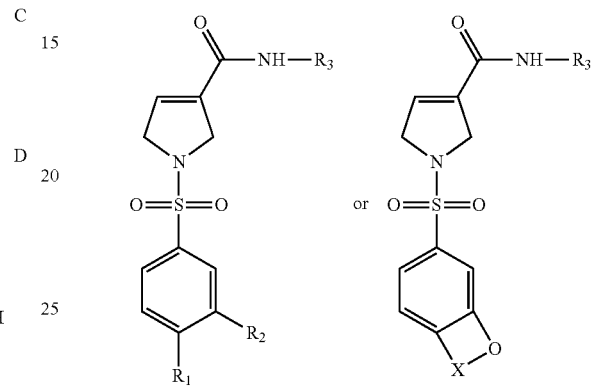

wherein $R_1$ is selected from hydrogen hydroxyl, cyano, halogen, carboxyl, $C_1$-$C_6$ alkyl, $C_1$-$C_6$ alkoxy, $C_2$-$C_6$ acylamino, $C_2$-$C_6$aminoacyl, $C_3$-$C_6$ heterocyclic radical, $C_3$-$C_6$ heterocyclic alkenyl or phenoxy;

$R_2$ is selected from hydrogen, hydroxyl, cyano, halogen, carboxyl, $C_1$-$C_6$ alkyl, $C_1$-$C_6$ alkoxy, $C_2$-$C_6$ acylamino, $C_2$-$C_6$ aminoacyl, $C_3$-$C_6$ heterocyclic radical, $C_3$-$C_6$ heterocyclic alkenyl, phenoxy, phenyl or substituted phenyl;

$R_3$ is selected from hydroxyl, amino-substituted phenyl, thiol or epoxy ketone groups:

X is selected from $$-\!\!\left(CH_2\right)_{\!m}\!-\quad or\quad -\!\!\left(CH_2\right)_{\!n}\!-O-$$

group, m is equal to 0, 1, 2 or 3, and n is equal to 0, 1 or 2.

Preferably, $R_1$ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl, Ethylaminoacyl, n-propylaminoacyl, isopropylaminoacyl, n-butylaminoacyl, isobutylaminoacyl, tert-butylaminoacyl, pentylaminoacyl, hexylaminoacyl, $C_3$ N-heterocyclic radical, $C_4$ N-heterocyclic radical, $C_5$ N-heterocyclic radical, $C_4$ N-heterocyclic radical, $C_3$ N-heterocyclic alkenyl, $C_4$ N-heterocyclic alkenyl, $C_5$ N-heterocyclic alkenyl, $C_6$ N-heterocyclic alkenyl or phenoxy;

$R_2$ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl, Ethylaminoacyl, n-propylaminoacyl, isopropylaminoacyl, n-butylaminoacyl, isobutylaminoacyl, tert-butylaminoacyl, pentylaminoacyl, hexylaminoacyl, $C_3$ N-heterocyclic radical, $C_4$ N-heterocyclic radical, $C_5$ N-heterocyclic radical, $C_6$ N-heterocyclic radical, $C_3$ N-heterocyclic alkenyl, $C_4$ N-heterocyclic alkenyl, $C_5$ N-heterocyclic alkenyl, $C_6$ N-heterocyclic alkenyl, phenoxy, phenyl or substituted phenyl;

$R_1$ and $R_2$ are not simultaneously hydrogen;

$R_3$ is selected from hydroxyl, amino-substituted phenyl or thiol;

m is equal to 1 or 2, and n is equal to 1 or 2.

Preferably, the compound shown as the formula I refers to:

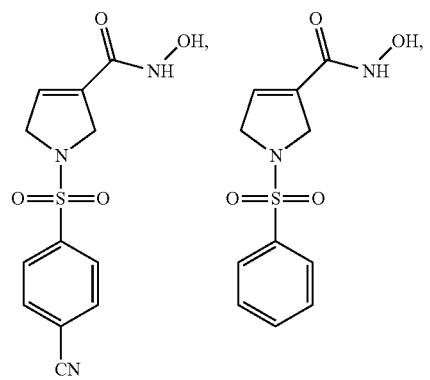

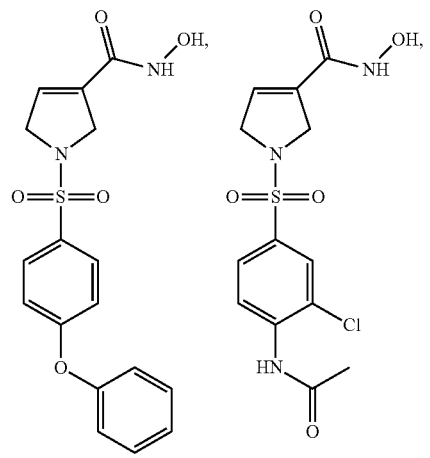

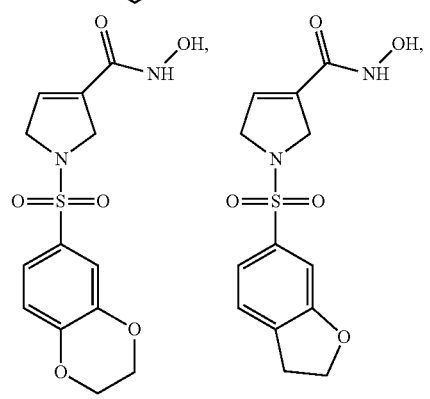

-continued

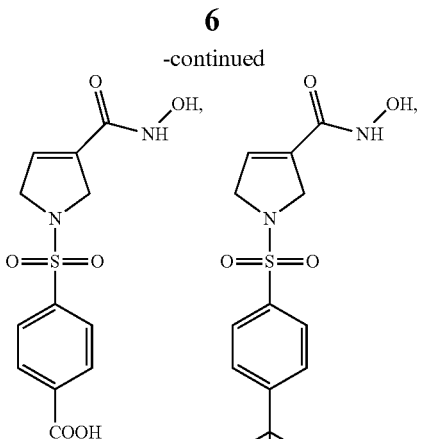

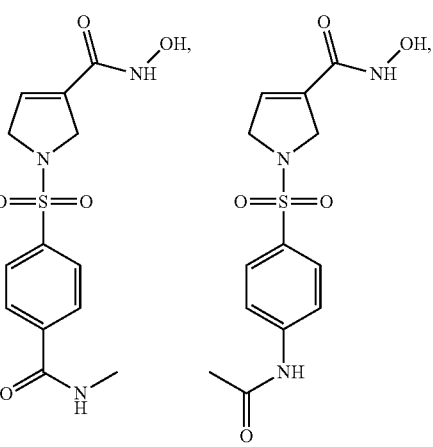

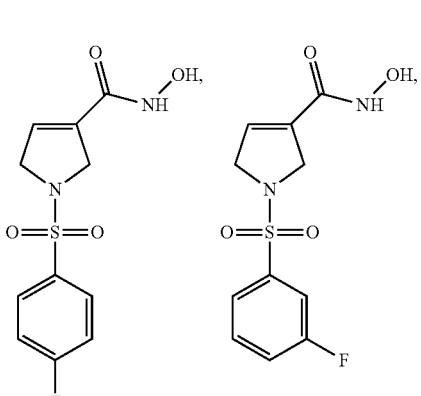

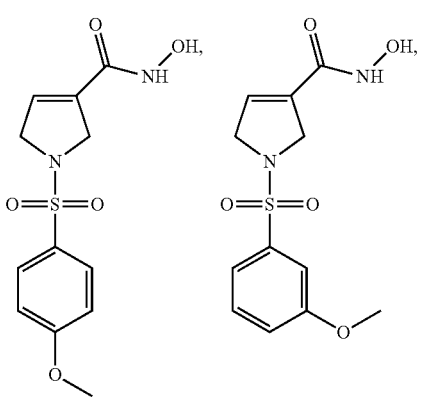

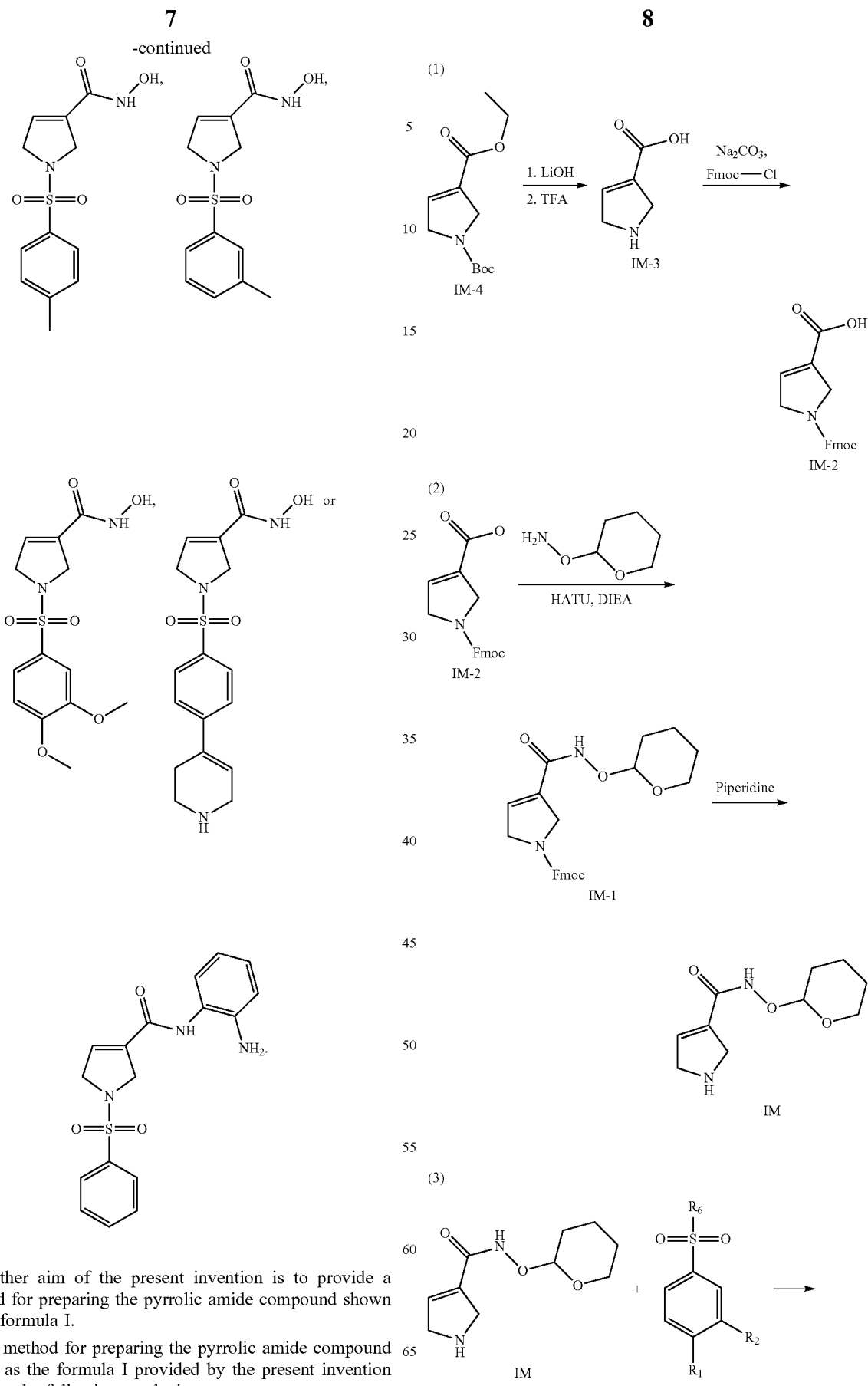
Another aim of the present invention is to provide a method for preparing the pyrrolic amide compound shown as the formula I.
The method for preparing the pyrrolic amide compound shown as the formula I provided by the present invention includes the following synthetic routes:

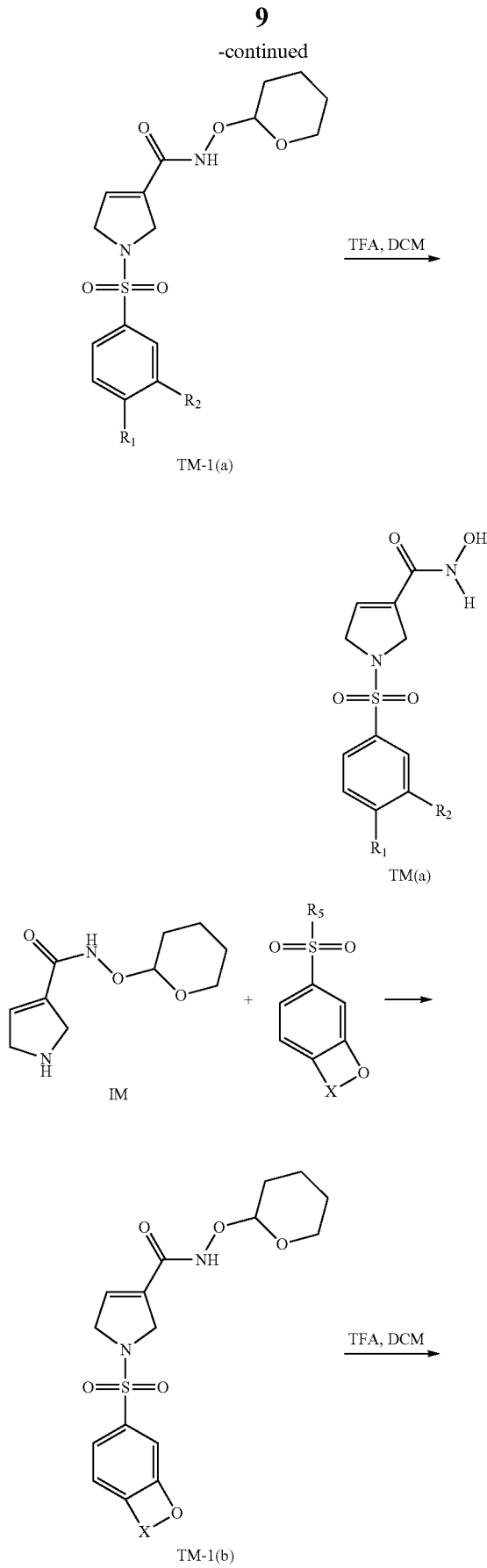

TM-1(a)

TM(a)

IM

TM-1(b)

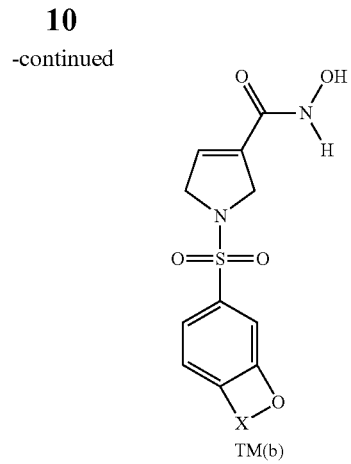

TM(b)

wherein Boc represents t-butyloxycarboryl; TFA represents trifluoroacetic acid; Fmoc-Cl represents fluorenone formyl chloride; HATU represents 2-(7-azobenzotriazole)-N,N,N'N'-tetramethyluronium hexafluorophosphate; DIEA represents the N,N-ethyldiisopropylamine; and DCM represents dichloromethane;

$R_1$ is selected from hydrogen, hydroxyl, cyano, halogen, carboxyl, $C_1$-$C_6$ alkyl, $C_1$-$C_6$ alkoxy, $C_2$-$C_6$ acylamino, $C_2$-$C_6$ aminoacyl, $C_3$-$C_6$ heterocyclic radical, $C_3$-$C_6$ heterocyclic alkenyl or phenoxy;

$R_2$ is selected from hydrogen, hydroxyl, cyano, halogen, carboxyl, $C_1$-$C_6$ alkyl, $C_1$-$C_6$ alkoxy, $C_2$-$C_6$ acylamino, $C_2$-$C_6$ aminoacyl, $C_3$-$C_6$ heterocyclic radical, $C_3$-$C_6$ heterocyclic alkenyl, phenoxy, phenyl or substituted phenyl;

$R_5$ is selected from halogen;

X is selected from

—(CH$_2$)$_m$— or —(CH$_2$)$_n$—O— group, m is equal to 0, 1, 2 or 3, and n is equal to 0, 1 or 2.

The method comprises the following steps:

a, after stirring a compound IM-4, lithium hydroxide and a mixed solvent of ether solvents or water at a temperature of 20° C.-30° C. to react for 1-6 hours, removing an organic solvent, adding water for diluting, regulating the pH value to 3-6, separating out solids, filtering to obtain solids; washing the solids with water and drying the solids, thereby obtaining N-t-butyloxycarboryl-2,5-dihydro-1H-pyrrole-3-formic acid, wherein a molar ratio of the compound IM-4 to the lithium hydroxide is (1):(1-10); a mass-volume ratio of the compound IM-4 to the mixed solvent is (1):(7-20) (m:v); and a volume ratio of the ether solvents to the water in the mixed solvent is (1-2):1;

b, dissolving the N-t-butyloxycarboryl-2,5-dihydro-1H-pyrrole-3-formic acid in the step a in a halocarbon solvent at a temperature of 0° C.-5° C., adding trifluoroacetic acid, and stirring at the temperature of 20° C.-30° C. to react for 2-12 hours to obtain a reaction solution; and concentrating the reaction solution to obtain a yellow oily matter, that is, a compound IM-3, wherein a mass-volume ratio of the N-t-butyloxycarboryl-2,5-dihydro-1H-pyrrole-3-formic acid to the halocarbon solvent to the trifluoroacetic acid is (1):(5-20):(2-10)(m:v:v);

c, after stirring the compound IM-3 in the step b, sodium carbonate, fluorenone formyl chloride and the mixed solvent of the ether solvents and the water at the temperature of 20°

C.-30° C. to react for 12-16 hours, adding water for diluting, regulating the pH value to 1-3, extracting with the ester solvents, merging an organic phase, and drying, filtering and concentrating the organic phase to obtain a compound IM-2, wherein a molar ratio of the compound IM-3 to the sodium carbonate to the fluorenone formyl chloride is (1): (1-5):(0.9-1.5); a mass-volume ratio of the compound IM-3 to the mixed solvent is (1):(10-25); and a volume ratio of the ether solvents to the water in the mixed solvent is (1-2):(1);

d, after stirring the compound IM-2 in the step c, O-(tetrahydro-2H-pyran-2-yl) hydramine, 2-(7-azobenzotriazole)-N,N,N',N'-tetramethyluronium hexafluorophosphate, N,N-ethyldiisopropylamine and halocarbon solvents at a temperature of 25° C.-30° C. to react for 12-16 hours, adding water for diluting, extracting with the ester solvents, merging the organic phase, and drying, filtering and concentrating the organic phase to obtain a crude product, purifying the crude product through column chromatography, thereby obtaining a compound IM-1, wherein a molar ratio of the compound IM-2 to the O-(tetrahydro-2H-pyran-2-yl) hydramine to the 2-(7-azobenzotriazole)-N,N,N',N'-tetramethyluronium hexafluorophosphate to the N,N-ethyldiisopropylamine is (1):(1 -2): (1-2):(2-4); and a mass-volume ratio of the compound. IM-2 to the halocarbon solvents is (1):(9-20):(m:v);

e, after stirring the compound IM-1 in the step d, piperidine and nitrogen-containing solvents at die temperature of 25° C.-30° C. react for 4-6 hours, adding water for diluting, extracting with the ester solvents, merging the organic phase, and drying, filtering and concentrating the organic phase, thereby obtaining a compound IM, wherein a mass-volume ratio of the compound IM-1 to the piperidine to the nitrogen-containing solvents is (1):(1-4): (5-20);

f, after stirring the compound IM in the step e, triethylamine,

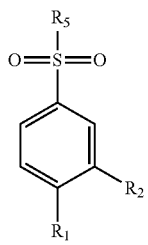

and the halocarbon solvents at the temperature of 25° C.-30° C. to react for 1-10 hours, removing the solvents to obtain a crude product, purifying the crude product through the column chromatography, thereby obtaining a compound TM-1(a), wherein a molar ratio of the compound IM to the triethylamine to

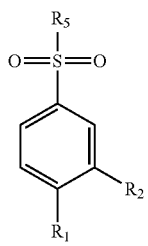

is (1):(1-5):(1-2), and a mass-volume ratio of the compound IM to the halocarbon solvents is (1):(50-100):(m:v);

or after stirring the compound IM in the step e, the triethylamine,

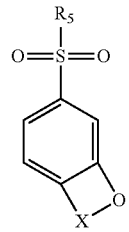

and the halocarbon solvents at the temperature of 25° C.-30° C. to react for 1-10 hours, removing the solvents to obtain a crude product, purifying the crude product through the column chromatography, thereby obtaining a compound TM-1(b), wherein a molar ratio of the compound IM to the triethylamine to

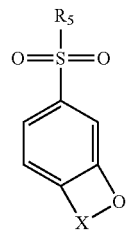

is (1):(1-5):(1-2), and a mass-volume ratio of the compound IM to the halocarbon solvents is (1):(5-100):(m:v); and g, after dissolving the compound TM-1(a) in the step f in the halocarbon solvents at the temperature of 0° C.-5° C., adding the trifluoroacetic acid and stirring at the temperature of 25° C.-30° C. to react for 1-12 hours, removing the solvents to obtain a crude product, purifying the crude product through preparative high performance liquid chromatography, thereby obtaining a compound TM(a), wherein a mass-volume ratio of the compound TM-1(a) to the halocarbon solvents to the trifluoroacetic acid is (1):(50-100): (10-50)(m:v:v);

or after dissolving the compound TM-1(b) the step f in the halocarbon solvents at the temperature of 0° C.-5° C., adding the trifluoroacetic acid and stirring at the temperature of 25° C.-30° C. to react for 1-12 hours, removing the solvents to obtain a crude product, purifying the crude product through the preparative high performance liquid chromatography, thereby obtaining a compound TM-1(b), wherein a mass-volume ratio of the compound TM-1(b) to the halocarbon solvents to the trifluoroacetic acid is (1):(50-100): (10-50)(m:v:v).

Preferably, the method comprises the following steps:

a, alter stirring the compound IM-4, the lithium hydroxide and the mixed solvent of the ether solvents and water at a temperature of 25° C. to react for 2 hours, removing the organic solvent, adding water for diluting, regulating the pH value to 5, separating out solids, filtering to obtain solids; washing the solids with water and drying the solids, thereby obtaining N-t-butyloxycarboryl-2,5-dihydro-1H-pyrrole-3-formic acid, wherein a molar ratio of the compound IM-4 to the lithium hydroxide is (1):(4.5-5); a mass-volume ratio of the compound IM-4 to the mixed solvent is (1):(10-12) (m:v); and a volume ratio of the ether solvents to the water in the mixed solvent is 2:1;

b, dissolving the N-t-butyloxycarboryl-2,5-dihydro-1H-pyrrole-3-formic acid in the step a in a halocarbon solvent at, a temperature of 0° C., adding trifluoroacetic acid, and stirring at the temperature of 25° C. to react for 2 hours to obtain a reaction solution; and concentrating the reaction solution to obtain a yellow oily matter, that is, the compound IM-3, wherein a mass-volume ratio of the N-t-butyloxycarboryl-2,5-dihydro-1H-pyrrole-3-formic acid to the halocarbon solvent to the trifluoroacetic acid is (1):(10):(4-5)(m:v:v);

c, after stirring the compound IM-3 in the step b, sodium carbonate, fluorenone formyl chloride and the mixed solvent of the ether solvents and the water and stirring at the temperature of 25° C. for 12-16 hours, adding water for diluting, regulating the pH value to 1, extracting with the ester solvents, merging an organic phase, and drying, filtering and concentrating the organic phase to obtain the compound IM-2, wherein a molar ratio of the compound IM-3 to the sodium carbonate to the fluorenone formyl chloride is 1:3:1; a mass-volume ratio of the compound IM-3 to the mixed solvent is 1:20: and a volume ratio of the ether solvents to the water in the mixed solvent is 5:3;

d, after stilling the compound IM-2 in the step c, O-(tetrahydro-2H-pyran-2-yl) hydramine, 2-(7-azobenzotriazole)-N,N,N',N'-tetramethyluronium hexafluorophosphate, N,N-ethyldiisopropylamine and halocarbon solvents at a temperature of 25° C. to react for 12-16 hours, adding water for diluting, extracting with the ester solvents, merging the organic phase, and drying, filtering and concentrating the organic phase to obtain a crude product, purifying the crude product through column chromatography, thereby obtaining the compound IM-1, wherein a molar ratio of the compound IM-2 to the O-(tetrahydro-2H-pyran-2-yl) hydramine to the 2 -(7-azobenzotriazole)-N,N,N',N'-tetramethyluronium hexafluorophosphate to the N,N-ethyldiisopropylamine is 1:1.1:1.2: 3; and a mass-volume ratio of the compound IM-2 to the halocarbon solvents is (1):(9-10):(m:v);

e, after stirring the compound IM-1 in the step d, piperidine and nitrogen-containing solvents at the temperature of 25° C. to react for 4-6 hours, adding water for diluting, extracting with the ester solvents, merging the organic phase, and drying, filtering and concentrating the organic phase, thereby obtaining the compound IM, wherein a mass-volume ratio of the compound IM-1 to the piperidine to the nitrogen-containing solvents is 1:2:10;

f, after stirring the compound IM in the step e, triethylamine,

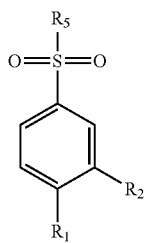

and the halocarbon solvents at the temperature of 25° C. to react for 2 hours, removing the solvents to obtain a crude product, purifying the crude product through the column chromatography, thereby obtaining, the compound TM-1(a), wherein a molar ratio of the compound IM to the triethylamine to

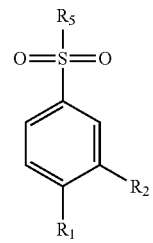

is (1):(1.4):(1-1.2), and a mass-volume ratio of the compound IM to the halocarbon solvents is 1.80 (m:v);

or after stirring the compound IM in the step e, the triethylamine,

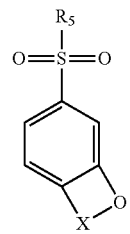

and the halocarbon solvents at the temperature of 25° C. to react for 2 hours, removing the solvents to obtain a crude product, purifying the crude product through the column chromatography, thereby obtaining a compound TM-1(b), wherein a molar ratio of the compound IM to the triethylamine to

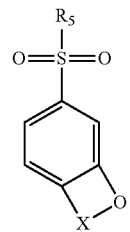

is (1):(1.4):(1-1.2), and a mass-volume ratio of the compound IM to the halocarbon solvents is (1):(80):(m:v); and g, after dissolving the compound TM-1(a) in the step f in the halocarbon solvents at the temperature of 0° C., adding the trifluoroacetic acid and stirring at the temperature of 25° C. to react for 2 hours, removing the solvents to obtain a crude product, and purifying the crude product through preparative high performance liquid chromatography, thereby obtaining the compound TM(a), wherein a mass-volume ratio of the compound TM-1(a) to the halocarbon solvents to the trifluoroacetic acid is (1):(60-65): (25)(m:v: v);

or after dissolving the compound TM-1(b) in the step f in the halocarbon solvents at the temperature of 0° C., adding the trifluoroacetic acid and stirring at the temperature of 25° C. to react for 2 hours, removing the solvents to obtain a crude product, and purifying the crude product through the preparative high performance liquid chromatography, thereby obtaining the compound TM(b), wherein a mass-volume ratio of the compound TM-1(b) to the halocarbon solvents to the trifluoroacetic acid is (1):(60-65): (25)(m:v:v).

Preferably, $R_1$ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl, Ethylaminoacyl, n-propylaminoacyl, isopropylaminoacyl, n-butylaminoacyl, isobutylaminoacyl, tert-butylaminoacyl, pentylaminoacyl, hexylaminoacyl, $C_3$ N-heterocyclic radical, $C_4$ N-heterocyclic radical, $C_5$ N-heterocyclic radical, $C_6$ N-heterocyclic radical, $C_3$ N-heterocyclic alkenyl, $C_4$ N-heterocyclic alkenyl, $C_5$ N-heterocyclic alkenyl, $C_6$ N-heterocyclic alkenyl or phenoxy;

$R_2$ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl. Ethylaminoacyl, n-propylaminoacyl, isopropylaminoacyl, n-butylaminoacyl, isobutylaminoacyl, tert-butylaminoacyl, pentylaminoacyl, hexylaminoacyl, $C_3$ N-heterocyclic radical, $C_4$ N-heterocyclic radical, $C_5$ N-heterocyclic radical, $C_6$ N-heterocyclic radical, $C_3$ N-heterocyclic alkenyl, $C_4$ N-heterocyclic alkenyl, $C_5$ N-heterocyclic alkenyl, $C_6$ N-heterocyclic alkenyl, phenoxy, phenyl or substituted phenyl, $R_1$ and $R_2$ are not simultaneously hydrogen;

$R_5$ is selected from fluorine, chlorine, bromine or iodine;

m is equal to 1 or 2, and n is equal to 1 or 2.

Preferably, the

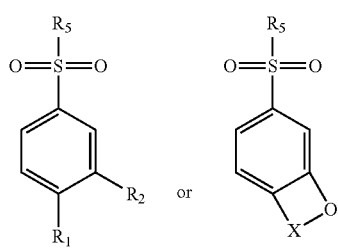

refers to:

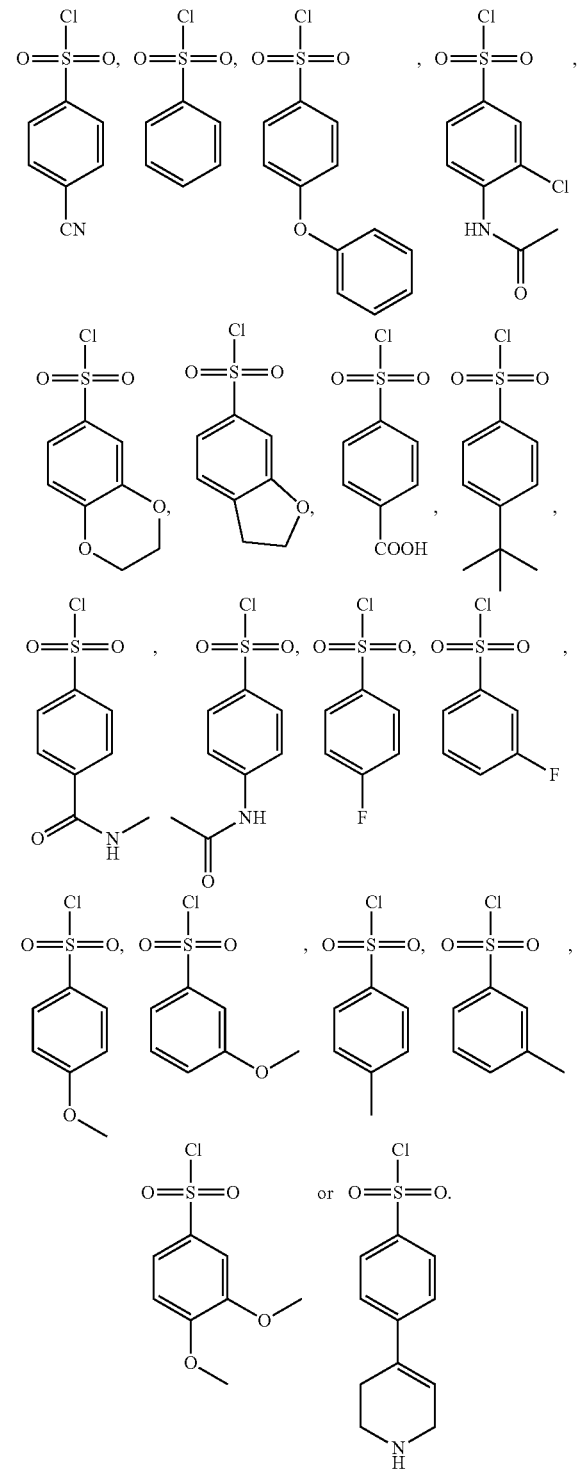

In the steps a-g, the ether solvents refer to any one or more of tetrahydrofuran, diethyl ether, tert-butyl methyl ether, isopropyl ether and butyl ether; the halocarbon solvents refer to any one or more of dichloromethane, chloroethane, dichloroethane, trichloromethane and carbon tetrachloride; the ester solvents refer to any one or more of ethyl acetate and ethyl formate: and the nitrogen-containing solvents refer to any one or more of N,N-dimethylformamide, N,N-dimethyl-acetamide, acetonitrile and pyridine.

The present invention further provides another method for preparing the pyrrolic amide compound shown as the formula I.

The method for preparing the pyrrolic amide compound shown as the formula I provided by the present invention includes the following synthetic routes:

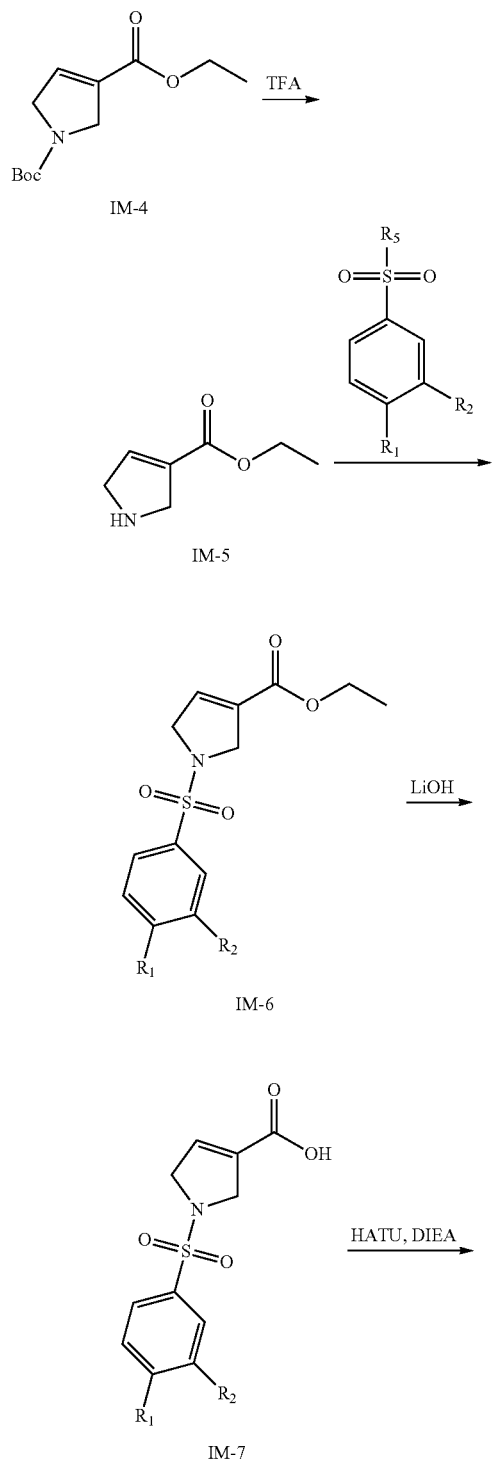

-continued

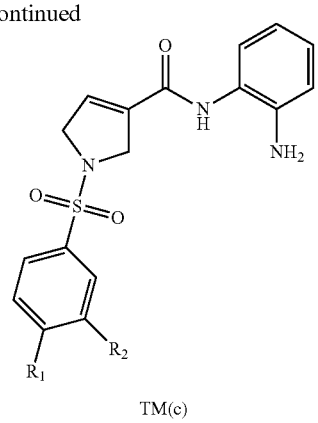

TM(c)

wherein Boc represents the t-butyloxycarboryl; TFA represents the trifluoroacetic acid; HATU represents the 2-(7-azobenzotriazole)-N,N,N',N'-tetramethyluronium hexafluorophosphate, DIEA represents the N,N-ethyldiisopropylamine; and LiOH represents the lithium hydroxide;

$R_1$ is selected from hydrogen, hydroxyl, cyano, halogen, carboxyl, $C_1$-$C_6$ alkyl, $C_1$-$C_6$ alkoxy, $C_2$-$C_6$ acylamino, $C_2$-$C_6$ aminoacyl, $C_3$-$C_6$ heterocyclic radical, $C_3$-$C_6$ heterocyclic alkenyl or phenoxy;

$R_2$ is selected from hydrogen, hydroxyl, cyano, halogen, carboxyl, $C_1$-$C_6$ alkyl, $C_1$-$C_6$ alkoxy, C-2-$C_6$ acylamino, $C_2$-C6 aminoacyl, $C_3$-$C_6$ heterocyclic radical, $C_3$-$C_6$ heterocyclic alkenyl, phenoxy, phenyl or substituted phenyl;

$R_5$ is selected from halogen.

The method comprises the following steps:

① dissolving the compound IM-4 in a halocarbon solvent at a temperature of 0° C.-5° C., adding trifluoroacetic acid, and stirring at the temperature of 20° C.-30° C. to react for 2-12 hours to obtain a reaction solution; and concentrating the reaction solution to obtain a yellow oily matter, that is, a compound IM-5, wherein a mass-volume ratio of the compound IM-4 to the halocarbon solvent to the trifluoroacetic acid is (1):(5-20):(2-10);

② stirring the compound IM-5 in the step ① triethylamine,

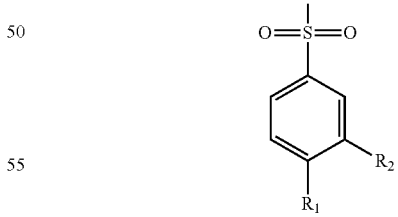

and the halocarbon solvents at the temperature of 25° C.-30° C. to react for 1-10 hours, adding water for carrying out a quenching reaction to obtain a reaction solution; extracting the reaction solution by using the ester solvents, merging the organic phase, washing the organic phase by using a saturated salt solution, drying, filtering and concentrating the organic phase to obtain a crude product, purifying the crude product through column chromatography, thereby obtaining a compound IM-6, wherein a molar ratio of the compound IM-5 to the triethylamine to

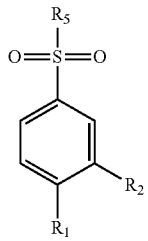

is (1):(1-5):(1-2), and a mass-volume ratio of the compound IM-5 to the halocarbon solvents is (1):(50-100) (m:v);

③ stirring the compound IM-6 in the step ② lithium hydroxide and a mixed solvent of ether solvents and water at a temperature of 20° C.-30° C. to react for 10-16 hours to obtain a reaction solution, regulating the pH value of the reaction solution to 1-5, extracting with the ester solvents, merging the organic phase, and drying, filtering and concentrating the organic phase, thereby obtaining a compound IM-7, wherein a molar ratio of the compound IM-4 to the lithium hydroxide is (1):(1-10); a mass-volume ratio of the compound IM-4 to the mixed solvent is (1):(55-60):(m:v); and a volume ratio of the ether solvents to the water in the mixed solvent is (1-5):1; and ④ stirring the compound IM-7 in the step ③ 1,2-diaminobenzene, 2 -(7-azobenzotriazole) -N,N,N',N'-tetramethyluronium hexafluorophosphate, N,N-ethyldiisopropylamine and halocarbon solvents at a temperature of 25° C.-30° C. to react for 12-16 hours to obtain a reaction solution, diluting the reaction solution by using water, extracting with the ester solvents, merging the organic phase, drying, filtering and concentrating the organic phase to obtain a crude product, and purifying the crude product through column chromatography, thereby obtaining the compound TM(c), wherein a molar ratio of the compound IM-7 to the 1,2-diaminobenzene to the 2-(7-azobenzotriazole)-N,N,N',N'-tetramethyluronium hexafluorophosphate to the N,N-ethyldiisopropylamine is (1):(1-2):(1-2):(2-4); and a mass-volume ratio of the compound IM-7 to the halocarbon solvents is (1):(40-100) (m:v).

Preferably, the method comprises the following steps;

① dissolving the compound IM-4 in the halocarbon solvent at a temperature of 0° C., adding the trifluoroacetic acid, and stirring at the temperature of 25° C. to react for 2 hours to obtain a reaction solution; and concentrating the reaction solution to obtain a yellow oily matter, that is, the compound IM-5, wherein a mass-volume ratio of the compound IM-4 to the halocarbon solvent to the trifluoroacetic acid is 1:20:8:

② after stirring the compound IM-5 in the step ① triethylamine,

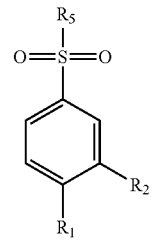

and the halocarbon solvents at the temperature of 25° C. to react for 2 hours, adding water for carrying out a quenching reaction to obtain a reaction solution; extracting the reaction solution by using the ester solvents, merging the organic phase, washing by using the saturated salt solution, drying, filtering and concentrating the organic phase to obtain a crude product, and purifying the crude product through the column chromatography, thereby obtaining the compound IM-6, wherein a molar ratio of the compound IM-5 to the triethylamine to

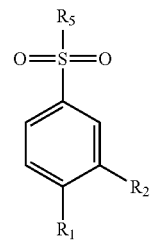

is (1):(2.5-3):(1.1-1.2), and a mass-volume ratio of the compound IM-5 to the halocarbon solvents is (1):(65-70) (m:v);

③ stirring the compound IM-6 in the step ② lithium hydroxide and the mixed solvent of the ether solvents and the water at a temperature of 25 ° C. to react for 12-16 hours to obtain a reaction solution, regulating the pH value of the reaction solution to 2, extracting with the ester solvents, merging the organic phase, and drying, filtering and concentrating the organic phase, thereby obtaining the compound IM-7, wherein a molar ratio of the compound IM-4 to the lithium hydroxide is 1:4.5; a mass-volume ratio of the compound IM-4 to then fixed solvent is (1);(55-60) (m:v); and a volume ratio of the ether solvents to the water in the mixed solvent is 3:1; and ④ stirring the compound IM-7 in the step ③ 1,2-diaminobenzene, 2-(7 -azobenzotriazole) -N,N,N',N'-tetramethyluronium hexafluorophosphate, N,N-ethyldiisopropylamine and the halocarbon solvents at a temperature of 25° C. to react for 12-16 hours to obtain a reaction solution, diluting the reaction solution with water, extracting with the ester solvents, merging the organic phase drying, filtering and concentrating the organic phase to obtain a crude product, and purifying the crude product through the column chromatography, thereby obtaining the compound TM(c), wherein a molar ratio of the compound IM-7 to the 1,2-diaminobenzene to the 2-(7-azobenzotriazole)-N,N,N', N'-tetramethyluronium hexafluorophosphate to the N,N-ethyldiisopropylamine is 1:1.5:1.5:3; and a mass-volume ratio of the compound IM-7 to the halocarbon solvents is (1): (40-45):(m:v).

Preferably,

R₁ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl, Ethylaminoacyl, n-propylaminoacyl, isopropylaminoacyl, n-butylaminoacyl, isobutylaminoacyl, tert-butylaminoacyl, pentylaminoacyl, hexylaminoacyl, $C_3$ N-heterocyclic radical, $C_4$ N-heterocyclic radical, $C_5$ N-heterocyclic radical, $C_6$ N-heterocyclic radical, $C_3$ N-heterocyclic alkenyl, $C_4$ N-heterocyclic alkenyl, $C_5$ N-heterocyclic alkenyl, $C_6$ N-heterocyclic alkenyl or phenoxy;

R₂ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl. Ethylaminoacyl, n-propylaminoacyl, isopropylaminoacyl, n-butylaminoacyl, isobutylaminoacyl, tert-butylaminoacyl, pentylaminoacyl, hexylaminoacyl $C_3$ N-heterocyclic radical, $C_4$ N-heterocyclic radical, $C_5$ N-heterocyclic radical, $C_6$ N-heterocyclic radical, $C_3$ N-heterocyclic alkenyl, $C_4$ N-heterocyclic alkenyl, $C_5$ N-heterocyclic alkenyl, $C_6$ N-heterocyclic alkenyl, phenoxy, phenyl or substituted phenyl;

R₁ and R₂ are not simultaneously hydrogen;

R₃ is selected from fluorine, chlorine, bromine or iodine.

Preferably, the

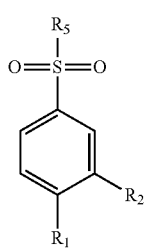

refers to:

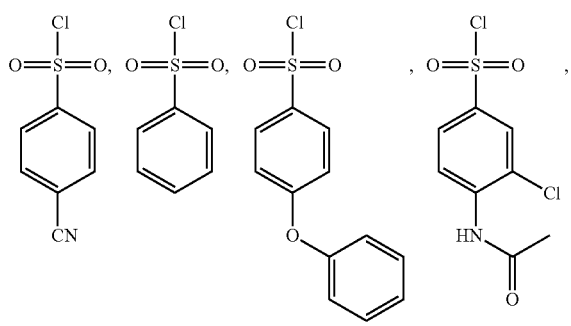

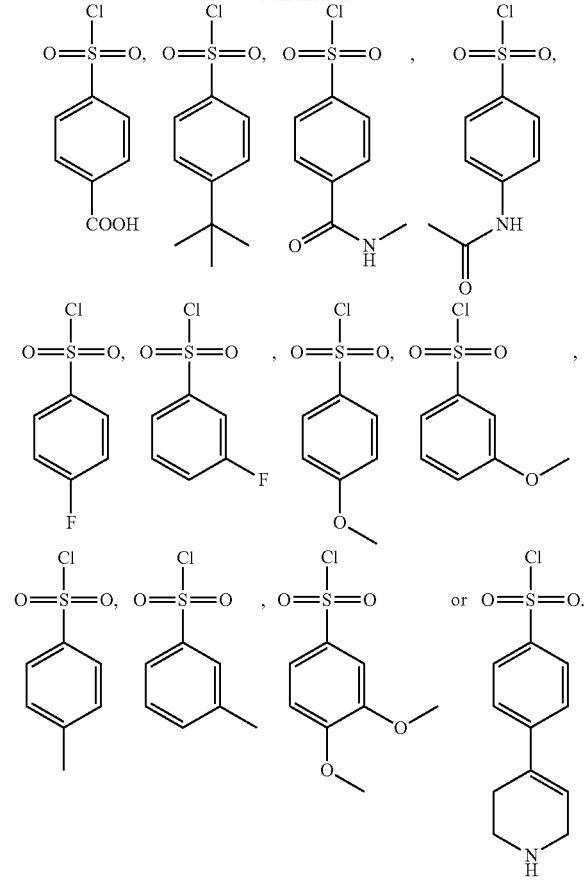

In the steps ①-④ the halocarbon solvents refer to any one or more of dichloromethane, chloroethane, dichloroethane, trichloromethane and carbon tetrachloride; the ester solvents refer to any one or more of ethyl acetate and ethyl formate; and the ether solvents refer to any one or more of tetrahydrofuran, diethyl ether, tert-butyl methyl ether, isopropyl ether and butyl ether.

The present invention thither provides an application of the pyrrolic amide compound or crystal forms thereof and the pharmaceutically acceptable salts, hydrates or solvates in preparation of histone deacetylase inhibitor medicines.

The histone deacetylase inhibitor medicines refer to medicines for treating diseases caused by histone deacetylase viability abnormality.

Further, the diseases refer to any one or more of cell proliferative diseases, autoimmune diseases, inflammations, neurodegenerative diseases or viral diseases.

Furthermore, the diseases refer to cancers.

A pharmaceutical composition for inhibiting the histone deacetylase viability, referring to a preparation prepared by taking the pyrrolic amide compound or crystal forms thereof and the pharmaceutically acceptable salts, hydrates or solvates as active ingredients and adding pharmaceutically common excipients or auxiliary ingredients.

Further, the preparation comprises an oral administration preparation, a sublingual administration preparation, a buccal administration preparation, a transdermal absorption preparation or an injection preparation.

The present invention provides a novel compound shown as a formula I, and the compound has high histone deacetylase inhibitory viability. Meanwhile, a method for preparing die novel compound in the present invention has the advantages of fewer steps, simple and convenient operation, safety, environment friendliness, high yield and the like and is very suitable for industrial application.

The following compounds 1-19 with high histone deacetylase inhibitory viabilities are prepared in the present invention, as shown in Table 1:

TABLE 1

Compounds 1-19 Prepared by the Present Invention

| Compound No. | Structure | Name |
|---|---|---|
| 1 | 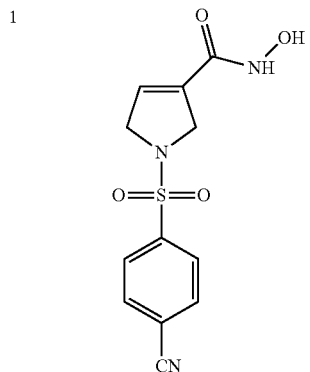 | N-hydroxy-1-((4-benzene-cyano)sulfonyl)2,5-dihydro-1H-pyrrole-3-formamide |
| 2 | 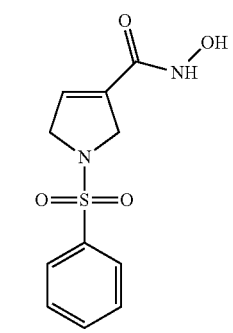 [SMILES: O=C(NO)C1=CCN(S(=O)(=O)c2ccccc2)C1] | N-hydroxy-1-(benzenesulfonyl)-2,5-dihydro-1H-pyrrole-3-formamide |
| 3 | 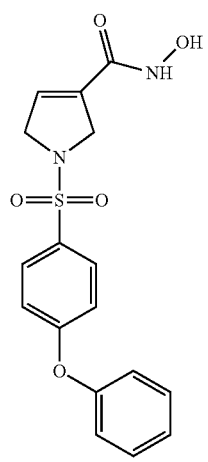 [SMILES: O=C(NO)C1=CCN(S(=O)(=O)c2ccc(Oc3ccccc3)cc2)C1] | N-hydroxy-1-(4-phenoxyphenyl)sulfonyl)-2,5-dihydro-1H-pyrrole-3-formamide |
| 4 | | N-hydroxy-1-((4-acetamido-3-chlorphenyl)sulfonyl)2,5-dihydro-1H-pyrrole-3-formamide |
| 5 | | N-hydroxy-1-((2,3-dihydro-benzo[b][1,4]dioxin)-6-sulfonyl)2,5-dihydro-1H-pyrrole-3-formamide |
| 6 | | N-hydroxy-1-((2,3-dihydro-benzofuran)-6-sulfonyl)2,5-dihydro-1H-pyrrole-3-formamide |

TABLE 1-continued

Compounds 1-19 Prepared by the Present Invention

| Compound No. | Structure | Name |
|---|---|---|
| 7 | | N-hydroxy-1-((4-formyl)-benzenesulfonyl)2,5-dihydro-1H-pyrrole-3-formamide |
| 8 | | N-hydroxy-1-((4-tert-butyl)phenyl)sulfonyl)2,5-dihydro-1H-pyrrole-3-formamide |
| 9 | | N-hydroxy-1-((4-(methylamine carbonyl)phenyl)sulfonyl)2,5-dihydro-1H-pyrrole-3-formamide |
| 10 | 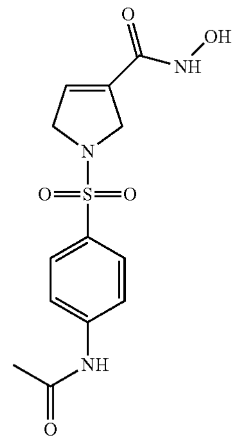 [SMILES: CC(=O)Nc1ccc(S(=O)(=O)N2CC=C(C(=O)NO)C2)cc1] | N-hydroxy-1-((4-acetamidophenyl)sulfonyl)2,5-dihydro-1H-pyrrole-3-formamide |
| 11 | 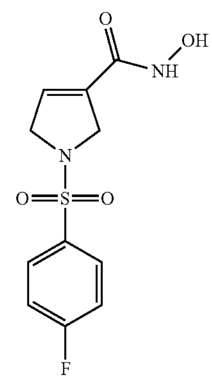 [SMILES: O=C(NO)C1=CCN(S(=O)(=O)c2ccc(F)cc2)C1] | N-hydroxy-1-((4-fluorophenyl)sulfonyl)2,5-dihydro-1H-pyrrole-3-formamide |
| 12 | 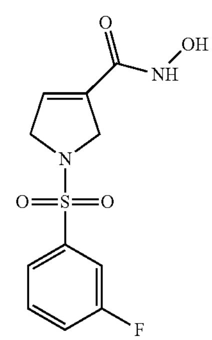 [SMILES: O=C(NO)C1=CCN(S(=O)(=O)c2cccc(F)c2)C1] | N-hydroxy-1-((3-fluorophenyl)sulfonyl)2,5-dihydro-1H-pyrrole-3-formamide |
| 13 | 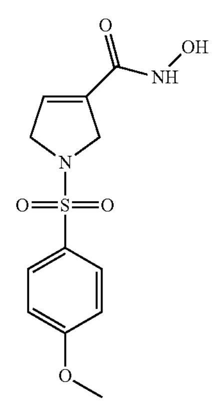 [SMILES: COc1ccc(S(=O)(=O)N2CC=C(C(=O)NO)C2)cc1] | N-hydroxy-1-((4-methoxyphenyl)sulfonyl)2,5-dihydro-1H-pyrrole-3-formamide |

TABLE 1-continued

Compounds 1-19 Prepared by the Present Invention

| Compound No. | Structure | Name |
|---|---|---|
| 14 | 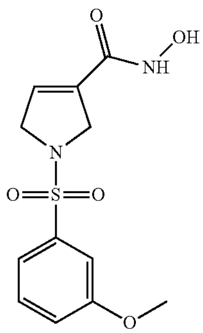 [SMILES: COc1cccc(S(=O)(=O)N2CC=C(C(=O)NO)C2)c1] | N-hydroxy-1-((3-methoxyphenyl)sulfonyl)2,5-dihydro-1H-pyrrole-3-formamide |
| 15 | 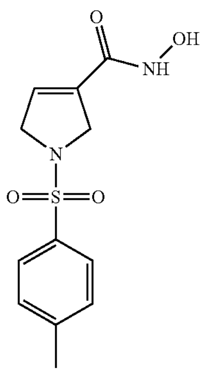 [SMILES: Cc1ccc(S(=O)(=O)N2CC=C(C(=O)NO)C2)cc1] | N-hydroxy-1-((4-methylphenyl)sulfonyl)2,5-dihydro-1H-pyrrole-3-formamide |
| 16 | 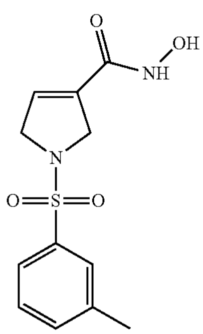 [SMILES: Cc1cccc(S(=O)(=O)N2CC=C(C(=O)NO)C2)c1] | N-hydroxy-1-((3-methylphenyl)sulfonyl)2,5-dihydro-1H-pyrrole-3-formamide |
| 17 | 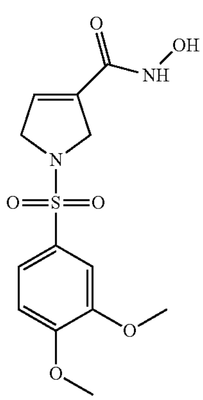 [SMILES: COc1ccc(S(=O)(=O)N2CC=C(C(=O)NO)C2)cc1OC] | N-hydroxy-1-((3,4-dimethoxyphenyl)sulfonyl)2,5-dihydro-1H-pyrrole-3-formamide |
| 18 | 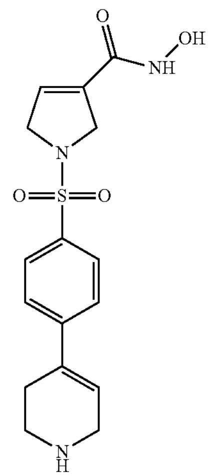 [SMILES: O=C(NO)C1=CCN(S(=O)(=O)c2ccc(C3=CCNCC3)cc2)C1] | N-hydroxy-1-((4-(1,2,3,6-tetrahydropyridine-4-yl)phenyl)sulfonyl)2,5-dihydro-1H-pyrrole-3-formamide |
| 19 | 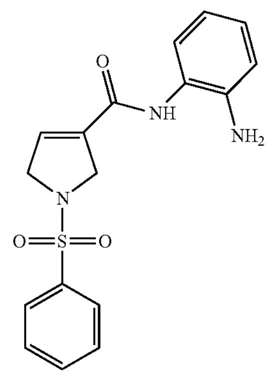 [SMILES: Nc1ccccc1NC(=O)C1=CCN(S(=O)(=O)c2ccccc2)C1] | N-(2-aminophenyl)-1-(benzenesulfonyl)-2,5-dihydro-1H-pyrrole-3-formamide |

Histone deacetylase plays an important role in gene transcription regulation, signal transduction, growth and development, differentiation and apoptosis, metabolic diseases, tumors and other physiological and pathological processes. If histone deacetylase viability is abnormal, a series of histone deacetylase viability abnormality diseases may be caused, including cell proliferative diseases, autoimmune diseases, inflammations neurodegenerative diseases or viral diseases (e.g., review of diseases applicable to HDAC6 inhibitors in the world patent WO2011011186).

The compounds and derivatives provided in the present invention can be named according to IUPAC (International Union of Pure and Applied Chemistry) or CAS (Chemical Abstracts Service, Columbus, Ohio) naming systems.

For definitions of terms used in the present invention: unless otherwise noted, initial definitions provided for groups or terms in the present invention are applicable to the groups or terms in the whole description; and for terms without specific definitions in the present invention, meanings which can be given to the terms by those skilled in the art should be provided according to the disclosure and context.

"Substitution" refers to that hydrogen atoms in molecules are substituted by other different atoms or molecules.

a minimum value and a maximum value of carbon atom content in hydrocarbon groups are expressed by prefixes. For example, a prefix (C a:-b) alkyl represents any alkyl containing "a" to "b" carbon atoms. Therefore, for example. (C1-4) alkyl refers to alkyl containing 1-4 carbon atoms.

A term "pharmaceutically acceptable" refers to that some carriers, carrying vehicles, diluents, excipients and/or formed salts are generally chemically or physically compatible with other ingredients forming dosage forms and are physiologically compatible with receptors.

Terms "salts" and "medicinal salts" refer to acidic and/or basic salts formed by the compounds or stereoisomers thereof and inorganic and/or organic acids and bases, and further include zwitterionic salts (inner salts) and quaternary ammonium salts, such as alkylammonium salts. These salts can be directly obtained in final separation and purification of the compounds, and can also be obtained by mixing the compounds above or stereoisomers thereof with a certain amount of acids or bases (such as equal equivalence) appropriately. These salts may be obtained by forming precipitates in solution and collected by a filtering method or by recovering after solvent evaporation, or prepared by performing freeze-drying operation after reacting in an aqueous medium. The salts in the present invention may be hydrochloride, sulfate, citrate, benzene sulfonate, hydrobromate, hydrofluoride, phosphate, acetate, propionate, succinate, oxalate, malate, succinate, fumarate, maleate, tartrate or trifluoroacetate of the compounds.

In some embodiments of the present invention, the present invention includes isotope labeled compounds, wherein the isotope labeled compounds are the same as the compounds listed in the present invention, but one or more atoms in the isotope labeled compounds are substituted by another atom. The atomic mass or mass number of the atom is different from common atomic mass or mass number in natural world. Isotopes in the compound shown as the formula (I) including hydrogen, carbon, nitrogen, oxygen, sulfur, that is, $^2H$, $^3H$, $^{13}C$, $^{14}C$, $^{15}N$, $^{17}O$, $^{18}O$, $^{35}S$ can be introduced. Compounds of the formula (I) containing the isotopes above and/or other atomic isotopes and stereoisomers thereof and medicinal salts of the compounds and stereoisomers may be included in the scope of the present invention.

Key intermediates and compounds in the present invention are separated and purified. A used manner refers to a common separation and purification method in organic chemistry, and examples of the method include filtration, extraction, drying, spin dry and various types of chromatography. Optionally, a next reaction can be carried out among the intermediates without purification.

In some embodiments, one or more compounds in the present invention can be combined with one another to use. The compounds in the present invention can be further selected to be combined with any other active reagents so as to be used for preparing medicines or pharmaceutical compositions for regulating cell functions or treating diseases. If a group of compounds are used, the compounds can simultaneously, individually or orderly perform administration on subjects.

Administration manners of the compounds or pharmaceutical compositions in the present invention are not specially limited. Representative administration manners include (but not limited to): oral, parenteral (intravenous, intramuscular or subcutaneous), and local administration.

Solid dosage forms used for oral administration include capsules, tablets, pills, powder and granules. In the solid dosage forms, active compounds are mixed with at least one conventional inert excipient (or carrier), such as sodium citrate or dicalcium phosphate, or are mixed with the following ingredients: (a) fillers or compatibilizers, such as starch, lactose, sucrose, glucose, mannitol and silicic acid; (b) adhesives such as hydroxymethyl cellulose, alginate, gelatin, polyvinyl pyrrolidone, sucrose and Arabic gum; (c) a wetting agent such as glycerin; (d) disintegrating agents, such as agar, calcium carbonate, potato starch or cassava starch, alginic acid, some composite silicates and sodium carbonate; (e) a slow-dissolving agent such as paraffin; (f) absorption accelerators such as quaternary ammonium compounds; (g) a wetting agent such as spermol and glycerin monostearate; (h) an adsorbent such as kaolin; and (i) lubricants such as talc, calcium stearate, magnesium stearate, solid polyethylene glycol, lauryl sodium sulfate or mixtures thereof. In the capsules, tablets and pills, the dosage forms may further include buffer agents.

The solid dosage forms such as the tablets, honeyed pills, capsules, pills and granules can be prepared from coatings and shell materials, such as casings and other known materials in the field. The solid dosage forms may include opacifying agents, and the active compounds or compounds in the compositions can be released in a certain part of a digestive tract in a delayed manner. Examples of available embedding ingredients refer to polymeric substances and wax substances. The active compounds can further form a microcapsule dosage form with one or more of the excipients when necessary.

Liquid dosage forms used for oral administration include pharmaceutically acceptable emulsion, solution, suspension, syrup or tinctures. In addition to the active compounds, the liquid dosage forms may include the conventional inert diluents used in the field, such as water or other solvents, solubilizers and emulsifiers, e.g. ethanol, isopropanol, ethyl carbonate, ethyl acetate, propylene glycol, 1,3-butanediol, dimethylformamide and oil, particularly cottonseed oil, peanut oil, maize germ oil, olive oil, castor oil and sesame oil or mixtures of the substances, etc.

In addition to the inert diluents, the composition may further include aids, such as wetting agents, emulsifiers, suspending agents, sweetening agents, flavoring agents and spices.

In addition to the active compounds, the suspension may include the suspending agent such as ethoxylated isooctadecanol, polyoxyethylenesorbitol, isosorbide dinitrate, microcrystalline cellulose, aluminum methoxide and agar or mixtures of the substances, etc.

A composition for parenteral infection may include physiologically acceptable sterile aqueous or anhydrous solution, dispersion, suspension or emulsion, and sterile powder redissolved into sterile injectable solution or dispersion. Appropriate aqueous and anhydrous carriers, diluents, solvents or excipients include water, ethanol, polyhydric alcohols and appropriate mixtures thereof.

Dosage forms of the compounds used for local administration in the present invention include ointments, powder, patches, spraying agents and inhalants. The active ingredients are mixed with physiologically acceptable carriers and any preservative or buffer agent or possibly needed propellants when necessary under sterile conditions.

The pharmaceutically acceptable excipients in the present invention refer to substances included in the dosage farms except the active ingredients.

The pharmaceutically acceptable auxiliary ingredients in the present invention have certain physiological viabilities, but the added ingredients do not change a leading role of the above pharmaceutical composition in a disease treatment process and only achieve auxiliary effects. The auxiliary effects only refer to utilization of known viabilities of the ingredients, and are conventional adjuvant treatment manners in the field of medicine. If the auxiliary ingredients above are matched with the pharmaceutical composition in the present invention, the auxiliary ingredients should still belong to the protection scope of the present invention.

The compounds in the present invention have viabilities of inducing differentiation, realizing immunoregulation, hindering cell cycle and promoting cell apoptosis and excellent HDAC subtype selectivity, aim to achieve better curative effects on various cancers, and simultaneously overcome toxic and side effects of the existing HDAC inhibitors, such as anemia, ischemic stroke, deep venous thrombosis, thrombocytopenia, emesis, etc.

The compounds in the present invention have HDAC inhibitory viabilities, can be used for treating diseases related to HDAC abnormal viability, and particularly have excellent effects on liver cancer.

Apparently, according to the above contents of the present invention, other modifications, replacements or changes in multiple forms can also be made according to general technical knowledge and common means in the field on premise of not deviating from the above basic technical thought of the present invention.

The above contents of the present invention are further described below in detail through specific implementation modes in a form of embodiments. However, it should not be understood that the scope of the above subject of the present invention is only limited to the following embodiments. All technologies realized based on the above contents of the present invention belong to the scope of the present invention.

DETAILED DESCRIPTION

Raw materials and devices used in specific embodiments of the present invention are known products and are obtained by purchasing commercially-available products.
Embodiment 1

Preparation of 1-(4-cyanobenzene)sulfonyl)-N-hydroxy-2,5-dihydro-1H-pyrrole-3-formamide 1. Preparation of 2,5-dihydro-1H-pyrrole-3-formic acid

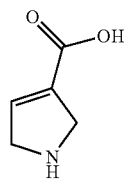

comprising the following steps: dissolving N-t-butyloxcarboryl-2,5-dihydro-1H-pyrrole-3-ethyl formate (8.5 g, 36 mmol; manufacturer: Accela ChemBio Co. Ltd.) in a mixed solution of 60 mL of tetrahydrofuran and 30 mL of water, and then adding lithium hydroxide (4.2 g, 176 mmol); after stirring at a temperature of 25° C. to react for 2 hours, removing an organic solvent in vacuum to obtain residues; adding a proper amount of water into the residues for diluting, regulating the pH value to 5 by using IN of hydrochloric acid, separating out solids, and filtering to obtain solids; washing the solids with water and thereby obtaining white solid N-t-butyloxycarboryl-2,5-dihydro-1H-pyrrole-3-formic acid (7.0 g, 93% yield);

MS(ESI)m/z214(m+1)$^+$.

dissolving N-t-butyloxycarboryl-2,5-dihydro-1H-pyrrole-3-formic acid (7 g, 36 mmol) in 70 mL of dichloromethane solution in an ice bath, dripping 30 mL of trifluoroacetic acid, stirring, slowly rising to the temperature of 25° C., and continuously stirring to react for 2 hours to obtain a reaction solution; and concentrating the reaction solution, thereby obtaining a yellow oily matter 2,5-dihydro-1H-pyrrole-3-formic acid(4.0 g, 99% yield);

MS(ESI)m/z114(M+1)$^+$.

2, Preparation of N-fluorenyloxycarbonyl-2,5-dihydro-1H-pyrrole-3-formic acid

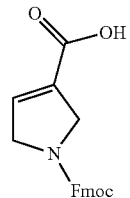

comprising the following steps: dissolving 2,5-dihydro-1H-pyrrole-3-formic acid (4.0 g, 35.4 mmol) it 50 mL of tetrahydrofuran and 30 mL of water; then adding sodium carbonate (11.2 g, 106 mmol) and fluorenone formyl chloride (9.2 g, 35.4 mmol; manufacturer; Alfa Aesar (China) Chemical Co., Ltd.); stirring at a temperature of 25° C. to react and stay overnight ("to react and stay overnight" in the present invention refers to that the reaction time is more than 8 hours at least); and adding 200 mL of water for diluting after reaction completion, regulating the pH value to 1 by using 2N of hydrochloric acid, extracting with ethyl acetate, merging an organic phase, drying, the organic phase, filtering and performing vacuum concentration, thereby obtaining white solid N-fluorenyloxycarbonyl-2,5-dihydro-1H-pyrrole-3-formic acid (11.0 g, 92% yield);

MS (EST) m/z336(M+1)$^+$.

3, Preparation of N-fluorenyloxycarbonyl-2,5-dihydro-1H-pyrrole-3-(tetrahydropyrane-2-oxo)-formamide

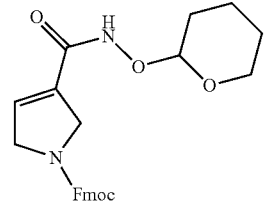

comprising Ire following steps: dissolving N-fluorenyloxycarbonyl-2,5-dihydro-1H-pyrrole-3-formic acid (11.0 g, 32.8 mmol) in 100 mL of dichloromethane, sequentially adding O-(tetrahydro-2H-pyran-2-yl)hydramine (4.2 g, 36 mmol), HATU (1.5 g, 39.4 mmol), DIEA (12.8 g, 98.4 mmol; manufacturer; J&K Scientific LTD.), stirring at a temperature of 25° C. to react and stay overnight to obtain a reaction solution; adding 50 mL of water into the reaction solution for diluting, extracting with ethyl acetate (50 mL×2), merging an ethyl acetate phase, drying the ethyl acetate phase, and filtering and concentrating to obtain a crude product; and purifying the crude product through column chromatography, thereby obtaining white solid N-fluorenyloxycarbonyl-2,5-dihydro-1H-pyrrole-3 -(tetrahydropyrane-2-oxo)-formamide(12 g, 48% yield);

MS (ESI) m/z435(M+1)⁻.

4. Preparation of 2,5-dihydro-1H-pyrrole-3-(tetrahydropyrane-2-oxo)-formamide

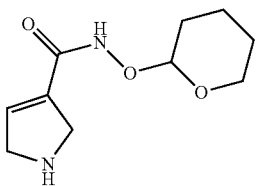 [SMILES: O=C(NOC1CCCCO1)C1=CCNC1]

comprising the following steps: dissolving N-fluorenyloxycarbonyl-2,5-dihydro-1H-pyrrole-3 -(tetrahydropyrane-2-oxo)-formamide (10 g, 23 mmol) in 100 mL of DMF; then adding 20 mL of piperidine, stirring at a temperature of 25° C. to react for 4 hours, adding 800 mL of water for diluting, extracting with ethyl acetate, and merging an organic phase; and drying, filtering and concentrating the organic phase, thereby obtaining white solid 2,5-dihydro-1H-pyrrole-3-(tetrahydropyrane-2-oxo)-formamide(4.5 g, 92% yield);

MS (ESI) m/z213(M+1)⁻.

5. Preparation of 1-((4-cyanobenzene)sulfonyl)-N-hydroxy-2,5-dihydro-1H-pyrrole-3-formamide

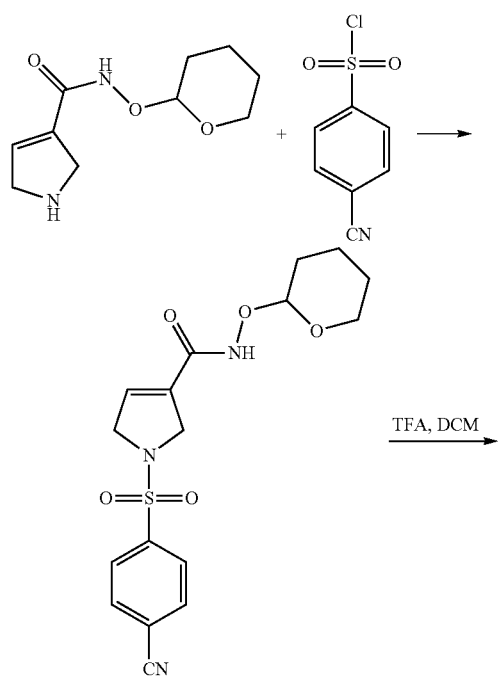

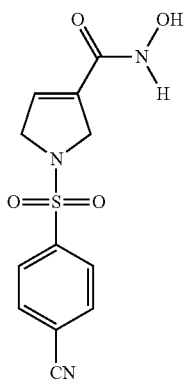

comprising the following steps:

Dissolving 2,5-dihydro-1H-pyrrole-3-(tetrahydropyrane-2-oxo)-formamide(100 mg,0.5 mmol) and triethylamine (66 mg, 0.7 mmol) in dichloromethane (8 mL), adding 4-cyanobenzene-1-sulfonyl chloride(125 mg, 0 5 mmol; manufacturer: J&K Scientific LTD.) into a reaction solution at a temperature of 25° C.; after stirring at the temperature of 25° C. to react for 2 hours, concentrating to remove a solvent to obtain crude product; and purifying the crude product through column chromatography, thereby obtaining white solid 1 -((4-cyanobenzene)sulfonyl)-N-((tetrahydro-2H-pyran-2-y)oxo)-2,5-dihydro-1H-pyrrole-3-formamide(80 mg, 39% yield);

dissolving 1-((4-cyanobenzene)sulfonyl)-N-((tetrahydro-2H-pyran-2-yl)oxo)-2,5 -dihydro-1H-pyrrole-3-formamide (80 mg, 0.3 mmol) in 5 mL of dichloromethane solution in an ice bath, dripping 2 mL of trifluoroacetic acid, stirring, slowly rising to a temperature of 25° C., and continuously stirring to react for 2 hours, concentrating to remove a solvent to obtain a crude product; and purifying the crude product through preparative high performance liquid chromatography, thereby obtaining white solid 1-((4-cyanobenzene)sulfonyl)-N-hydroxy-2,5-dihydro-1H-pyrrole-3-formamide (13 mg, 25% yield).

MS (ESI)m/z294(M+1)⁺.

1HNMR (400 MHz. DMSO-d6) δ10.80 (br s. 1H). 8.13-8.11 (m, 2H), 8.02-8.00 (m, 2H), 6.32 (s, 1H). 422-4.21 (d, J=2.4 Hz. 4H).

Embodiment 2

Preparation of N-hydroxy-1-(benzenesulfonyl)-2,5-dihydro-1H-pyrrole-3-formamide

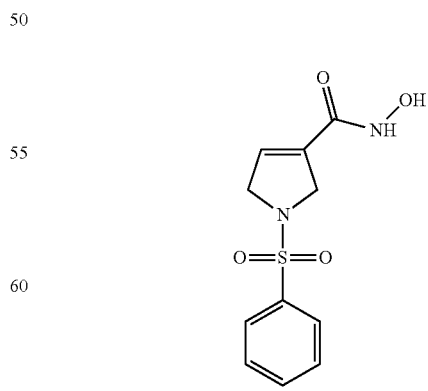

comprising the following step: preparing white solid N-hydroxy-1-(benzenesulfonyl)-2,5-dihydro-1H-pyrrole-3-formamide(18 mg, 14% yield) according to similar steps in embodiment 1 by taking 2,5-dihydro-1H-pyrrole-3-(tetrahydropyrane-2-oxo)-formamide (100 mg, 0 5 mmol) and benzene sulfonyl chloride (100 mg, 0.6 mmol; manufacturer: J&K Scientific LTD.) as raw materials;

MS (ESI)m/z269(M+1)+.

$^1$HNMR (400 MHz, DMSO-d$_6$)δ10.80(br s, 1H),9.0(br s, 1H), 7.84-7.82(d,J=7.6 Hz,2H), 7.74-7.70(m, 1H), 7.66-7.62 (m, 2H), 6.30 (s, 1H), 4.17(s, 4H).

Embodiment 3

Preparation of N-hydroxy-1((4-phenoxyphenyl)sulfonyl)-2,5-dihydro-1H-pyrrole-3-formamide

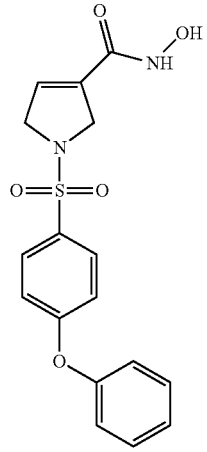 [SMILES: O=C(NO)C1=CCN(S(=O)(=O)c2ccc(Oc3ccccc3)cc2)C1]

comprising the following step: preparing white solid N-hydroxy-1((4-(trifluoromethoxy)phenyl)sulfonyl)-2,5-dihydro-1H-pyrrole-3-formamide (26 mg 16 yield) according to similar steps in embodiment 1 by taking 2,5-dihydro-1H-pyrrole-3-(tetrahydropyrane-2-oxo)-formamide (100 mg 0.5 mmol) and 4-phenoxybenzenesulfonyl chloride (125 mg, 0.6 mmol; manufacturer: J&K Scientific LTD.) as raw materials;

MS (ESI) m/z361 (M+1)+.

$^1$HNMR(400 MHz, DMSO-d$_6$) δ 10.82(br s, 1H), 9.02(br s, 1H), 7.84-7.82(m, 2H), 7.50-7.46(m, 2H),7.30-7.26(m, 1H), 7.18-7.12(m, 4H), 6.34(s, 1H), 4.16(s, 4H).

Embodiment 4

Preparation of N-hydroxy-1-((4-acetamido-3-chlorphenyl)sulfonyl)2,5-dihydro-1H-pyrrole-3-formamide

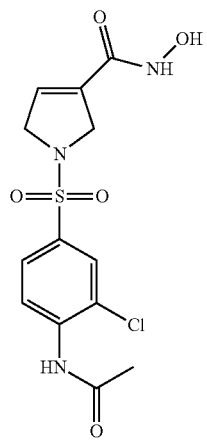 [SMILES: CC(=O)Nc1ccc(S(=O)(=O)N2CC=C(C(=O)NO)C2)cc1Cl]

comprising the following step: preparing white solid N-hydroxy-1-((4-acetamido-3-chlorphenyl)sulfonyl)2,5-dihydro-1H-pyrrole-3-formamide (47 mg, 10.7% yield) according to similar steps in embodiment 1 by taking 2,5-dihydro-1H-pyrrole-3-(tetrahydropyrane-2-oxo)-formamide (100 mg, 0.5 mmol) and 4-acetamido-3-chlorobenzenesulfonyl chloride (150 mg, 0.6 mmol; manufacturer J&K. Scientific LTD.) as raw materials;

MS (ESI) m/z360(M+1)+.

$^1$HNMR(400 MHz, CD$_2$OD) δ 8.25-8.23(d, J=8.8 Hz, 1H), 7.74(d, J=0.8 Hz, 1H), 7.80-7.78(m, 1H), 6.38(s, 1H), 4.28(s, 4H),2.25(s, 3H).

Embodiment 5

Preparation of N-hydroxy-1-((2,3-dihydrobenzo[b][1,4]dioxin)-6-sulfonyl)2,5-dihydro-1H-pyrrole-3-formamide

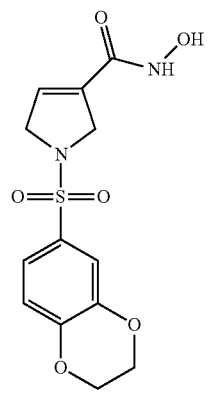 [SMILES: O=C(NO)C1=CCN(S(=O)(=O)c2ccc3c(c2)OCCO3)C1]

comprising the following step: preparing white solids N-hydroxy-1-((2,3-dihydrobenzo[b][1,4]dioxin)-6-sulfonyl)2,5-dihydro-1H-pyrrole-3-formamide (12 mg., 8.0% yield) according to similar steps in embodiment 1 by taking 2,5-dihydro-1H-pyrrole-3-(tetrahydropyrane-2-oxo)-formamide (100 mg, 0.5 mmol) and 2,3-dihydrobenzo[b][1,4]dioxin-6-sulfonyl chloride (132 mg, 0.6 mmol; manufacturer: J&K Scientific LTD.) as raw materials;

MS (ESI) m/z327(M+1)+.

$^1$HNMR(400 MHz, DMSO-d$_6$) δ 10.80(s, 1H), 9,05(br s, 1H), 7.31-7,26(m, 2H), 7.09-7.07(d, J=8.4 Hz, 1H), 632 (s, 1H), 4.34-43.1(m, 4H),4.14(s, 4H).

Embodiment 6

Preparation of N-hydroxy-1-((2,3-dihydrobenzofuran)-6-Sulfonyl)2,5-dihydro-1H-pyrrole-3-formamide

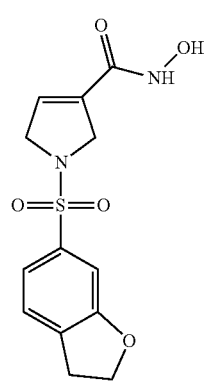 [SMILES: O=C(NO)C1=CCN(S(=O)(=O)c2ccc3c(c2)OCC3)C1]

comprising the following step: preparing white solid N-hydroxy-1-((2,3-dihydrobenzofuran)-6-sulfonyl)2,5-dihydro-1H-pyrrole:-3-formamide (10 mg 6.8% yield) according to similar steps in embodiment 1 by taking 2,5-dihydro-1H-pyrrole-3-(tetrahydropyrane-2-oxo)-formamide (100 mg, 0.5 mmol) and 2,3-dihydrobenzofuran-6-sulfonylchloride (123 mg, 0.6 mmol; manufacturer: J&K Scientific LTD.) as raw materials;

MS (ESI) m/z311(M+1)+.

$^1$HNMR(400 MHz, DMSO-d$_6$) δ 10.82(s, 1H), 9,05(br s, 1H), 7.69(d, J=1.6 Hz, 1H),7.59-7.57(m, 1H),6.96-6.94(d, J=8.4 Hz, 1H),6.31 (s, 1H),4.67-4.62(t, J=8.8 Hz, 2H)4.13(s, 4H), 3.29-3.24), (t, J=8.8 Hz, 2H).

Embodiment 7

Preparation of N-hydroxy-1-((4-formyl)-benzenesulfonyl)2,5-dihydro-1H-pyrrole-3-formamide

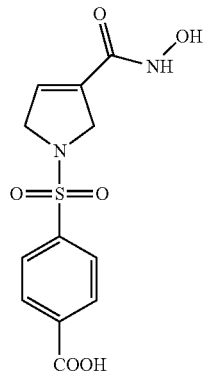 [SMILES: O=C(NO)C1=CCN(S(=O)(=O)c2ccc(C(=O)O)cc2)C1]

comprising the following step: preparing white solid N-hydroxy-1-((4-formyl)-benzenesulfonyl)2,5-dihydro-1H-formamide (116 mg, 79% yield) according to similar steps in embodiment 1 by taking 2,5-dihydro-1H-pyrrole-3-(tetrahydropyrane-2-oxo)-formamide (100 mg, 0.5 mmol) and 4-(chlorosulfonyl) benzoic acid (124 mg, 0.6 mmol; manufacturer: J&K Scientific LTD.) as raw materials;

MS (ESI) m/z313(M+1)+.

$^1$HNMR(400 MHz, DMSO-d$_6$) δ 10.81 (br s, 1H), 9.05(br s, 1H),8.16-8.14 (d, J=8.4 Hz, 2H), 7.96-7.94(d, J=8.4 Hz, 3H), 6.32(s, 1H), 4.40 (s, 4H).

Embodiment 8

Preparation of N-hydroxy-1-((4-(tert-butyl)phenyl)sulfonyl)2,5-dihydro-1H-pyrrole-3-formamide

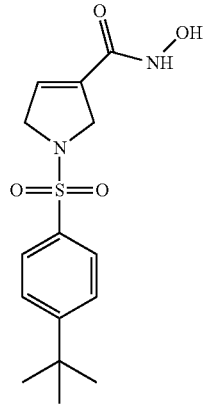 [SMILES: CC(C)(C)c1ccc(S(=O)(=O)N2CC=C(C(=O)NO)C2)cc1]

comprising the following step: preparing white solid N-hydroxy-1-((4-(tert-butyl)phenyl)sulfonyl)2,5-dihydro-1H-pyrrole-3-formamide (10 mg, 6% yield) according to similar steps in embodiment 1 taking 2,5 -dihydro-1H-pyrrole-3-(tetrahydropyrane-2-oxo)-formamide (100 mg, 0.5 mmol) and 4-(tert-butyl)phenyl)sulfonyl chloride (130 mg, 0.6 mmol; manufacturer J&K Scientific LTD.) as raw materials;

MS (ESI) m/z325(M+1)+.

$^1$HNMR(400 Hz, CD$_3$OD) δ 7.81-7.79(m, 2H), 7.69-7.67 (m, 2H), 6.36(s, 1H), 4.26(s, 4H), 1.37(s, 9H).

Embodiment 9

Preparation of N-hydroxy-1-((4-(methylamine carbonyl)phenyl)sulfonyl)2,5-dihydro-1H-pyrrole-3-formamide

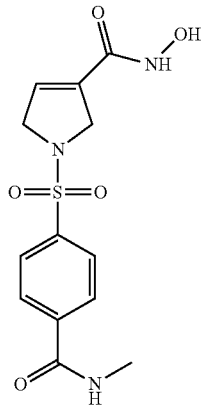 [SMILES: CNC(=O)c1ccc(S(=O)(=O)N2CC=C(C(=O)NO)C2)cc1]

comprising the following step: preparing white solid N-hydroxy-((4-methylamine carbonyl)phenyl)sulfonyl)2,5 -dihydro-1H-pyrrole-3-formamide(25 mg 16% yield) according to similar steps in embodiment 1 by taking 2,5-dihydro-1H-pyrrole-3-(tetrahydropyrane-2-oxo)-formamide (100 mg, 0.5 mmol) and 4-(methylamine carbonyl) benzene sulfonyl chloride (128 mg, 0.6 mmol; manufacturer: J&K Scientific LTD.) as raw materials;

MS (ESI) m/z326(M+1)+.

$^1$HNMR(400 MHz, DMSO-d$_6$)δ 11.81(br s, 1H), 9.05(br s, 1H)8.67(br s, 1H), 8.04-8.02 (d, J=8.4 Hz, 2H), 7.93-7.91 (d, J=8.4 Hz, 3H), 6.32(s, 1H), 4.20 (s, 4H).

Embodiment 10

Preparation of N-hydroxy-1-((4-acetamidophenyl)sulfonyl)2,5-dihydro-1H-pyrrole-3-formamide

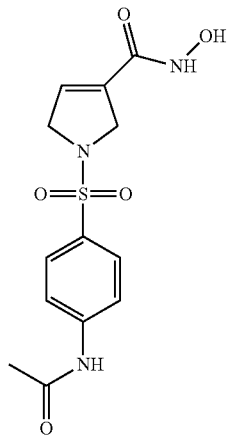 [SMILES: CC(=O)Nc1ccc(S(=O)(=O)N2CC=C(C(=O)NO)C2)cc1]

comprising the following step: preparing white solid N-hydroxy-1((4-acetamidophenyl)sulfonyl)2,5-dihydro-1H-pyrrole-3-formamide (15 mg, 9.6% yield) according to similar steps in embodiment 1 by taking 2,5-dihydro-1H-pyrrole-3-(tetrahydropyrane-2-oxo)-formamide (100 mg, 0.5 mmol) and 4-(acetamido) benzene sulfonyl chloride (128 mg, 0.6mmol; manufacturer: J&K Scientific LTD.) as raw materials;

MS (ESI) m/z326(M+1)⁻.

¹HNMR(400 MHz, CD3OD) δ 7.82(s, 4H), 6.38(s, 1H), 4.25(s, 4H), 2.17 (s, 3H).

Embodiment 11

Preparation of N-hydroxy-1-((4-fluorophenyl)sulfonyl)2,5-dihydro-1H-pyrrole-3-formamide

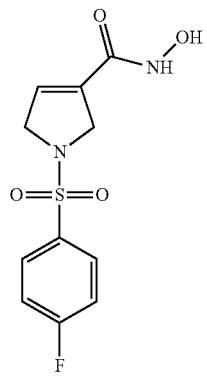 [SMILES: O=C(NO)C1=CCN(S(=O)(=O)c2ccc(F)cc2)C1]

comprising the following step: preparing white solid N-hydroxy-1-((4-fluorophenyl)sulfonyl)2,5-dihydro-1H-pyrrole-3-formamide (33 mg,25% yield) according to similar steps in embodiment 1 by taking 2,5-dihydro-1H-pyrrole-3-(tetrahydropyrane-2-oxo)-formamide (100 mg, 0.5 mmol) and 4-fluoro-benzene-sulfonyl chloride (109 mg, 0.6 mmol; manufacturer: J&K Scientific LTD.) as raw materials;

MS (ESI) m/z 287(M+1)⁺.

¹HNMR(400 Hz.,CD3OD) δ 7.96-7.93(d, J=4.8, 8.0 Hz, 2H),7.39-7.35(m, 2H), 6.4(s, 1H), 4.3(s, 4H).

Embodiment 12

Preparation of N-hydroxy-1-((3-fluorophenyl)sulfonyl)2,5-dihydro-1H-pyrrole-3-formamide

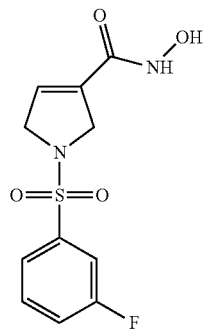 [SMILES: O=C(NO)C1=CCN(S(=O)(=O)c2cccc(F)c2)C1]

comprising the following step: preparing white solid N-hydroxy-1-((3-fluorophenyl)sulfonyl)2,5-dihydro-1H-pyrrole-3-formamide (33 mg,25% yield) according to similar steps in embodiment 1 by taking 2,5-dihydro-1H-pyrrole-3-(tetrahydropyrane-2-oxo)-formamide (100 mg,0.5 mmol) and 3-fluorobenzenesulfonyl chloride (109 mg, 0.6 mmol; manufacturer: J&K Scientific LTD.) as raw materials:

MS (ESI) m/z 287(M+1)⁺.

¹HNMR(400 Hz, CD3OD) δ 8.17-8.12 (m, J=8.0 Hz, 2H), 8.03-8.01(d, 1H), 7.89-7.85(m, 1H), 6.38(s, 1H) 4.31(s, 4H).

Embodiment 13

Preparation of N-hydroxy-1-((4-methoxyphenyl)sulfonyl)2,5-dihydro-1H-pyrrole-3-formamide

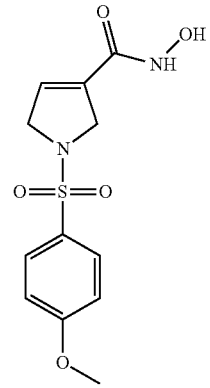 [SMILES: COc1ccc(S(=O)(=O)N2CC=C(C(=O)NO)C2)cc1]

comprising the following step: preparing white solid N-hydroxy-1-((4-methoxyphenyl)sulfonyl)2,5-dihydro-1H-pyrrole-3-formamide (34 mg, 23% yield) according to similar steps in embodiment 1 by taking 2,5-dihydro-1H-pyrrole-3-(tetrahydropyrane-2-oxo)-formamide (100 mg, 0.5 mmol) and 4-methoxybenzenesulfonyl chloride (123 mg, 0.6 mmol; manufacturer: J&K Scientific LTD.) as raw materials;

MS (ESI) m/z 299(M+1)⁺.

¹HNMR(400 Hz, CD3OD) δ=7.828-7.805(d, J=8 Hz, 2H), 7.145-7.123(d, J=8.8 Hz), 2H),6.432(s, 1H), 4.242(s, 4H), 3.896(s, 3H),

Embodiment 14

Preparation of N-hydroxy-1-((3-methoxyphenyl)sulfonyl)2,5-dihydro-1H-pyrrole-3-formamide

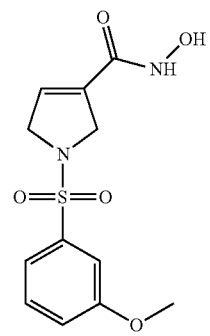 [SMILES: COc1cccc(S(=O)(=O)N2CC=C(C(=O)NO)C2)c1]

comprising the following steps: preparing white solid N-hydroxyl-1-((3-methoxyphenyl)sulfonyl)2,5-dihydro-1H-pyrrole-3-formamide (36 mg, 24% yield) according to similar steps m embodiment 1 by taking 2,5-dihydro-1H-pyrrole-3-(tetrahydropyrane-2-oxo)-formamide (100 mg, 0.5 mmol) and 3-methoxybenzenesulfonyl chloride (123 mg, 0.6 mmol; manufacturer: J&K Scientific LTD.) as raw materials;

LC-MS(ESI) m/z 299 (M+H)⁺.
¹HNMR (400 Hz, DMSO-D₆) δ 10.80(s, 1H), 9.02(s, 1H), 7.59-7.55(m, 1H), 7.41-7.39(d, J=8 Hz, 1H), 7.30-7.27(m, 2H), 6.35(s, 1H), 4.19(s, 4H), 3.85(s, 3H).

Embodiment 15

Preparation of N-hydroxy-1-((4-methylphenyl)sulfonyl)2,5-dihydro-1H-pyrrole-3-formamide

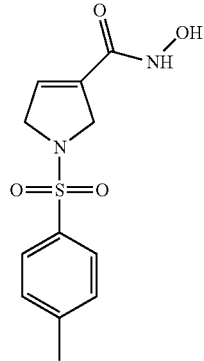 [SMILES: Cc1ccc(S(=O)(=O)N2CC=C(C(=O)NO)C2)cc1]

comprising the following steps: preparing white solid N-hydroxy-1-((4-methylphenyl)sulfonyl)2,5-dihydro-1H-pyrrole-3-formamide (26 mg, 19% yield) according to similar steps in embodiment 1 by taking 2,5 -dihydro-1H-pyrrole-3-(tetrahydropyrane-2-oxo)-formamide (100 mg,0.5 mmol) and 4-toluene sulfonyl chloride (114 mg, 0.6 mmol; manufacturer: J&K Scientific LTD.) as raw materials;

MS (ESI) m/z 283(M+1 )⁺.
¹HNMR (400 MHz, CD₃OD) δ=7.76 (d, J=8.4 Hz, 2H), 7.44 (d, J=8.0 Hz, 2H), 635 (s, 1H), 4.25 (s, 4H), 2.45 (s, 3H).

Embodiment 16

Preparation of N-hydroxy-1-((3-methylphenyl)sulfonyl)2,5-dihydro-1H-pyrrole-1H-3-formamide

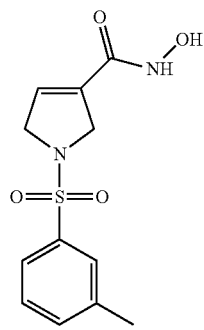 [SMILES: Cc1cccc(S(=O)(=O)N2CC=C(C(=O)NO)C2)c1]

comprising the following step: preparing white solid N-hydroxy-1-((3-methylphenyl)sulfonyl)2,5-dihydro-1H -pyrrole-3 -formamide (24 mg, 18% yield) according to similar steps in embodiment 1 by taking 2,5-dihydro-1H-pyrrole-3-(tetrahydropyrane-2-oxo)-formamide (100 mg,0.5 mmol) and 3-toluene sulfonyl chloride (114 mg, 0.6 mmol; manufacturer: J&K Scientific LTD.) as raw materials;

MS (ESI) m/z 283(M+1)⁺.
¹HNMR (400 MHz, CD₃OD) δ=7.70-7.66 (m, 2H), 7.52-7.51 (m, 2H), 6.36 (s, 1H), 4.26 (s. 4H), 2.46 (s, 3H).

Embodiment 17

Preparation of N-hydroxy-1-(3, 4-dimethoxyphenyl)sulfonyl)2,5-dihydro-1H-pyrrole-3-formamide

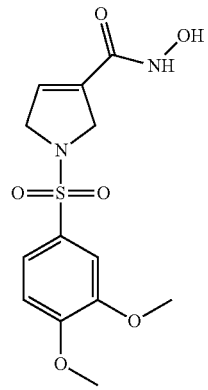 [SMILES: COc1ccc(S(=O)(=O)N2CC=C(C(=O)NO)C2)cc1OC]

comprising the following step: preparing white solid N-hydroxy-1-((3, 4-dimethoxyphenyl)sulfonyl)2,5-dihydro-1H-pyrrole-3-formamide (24 mg, 18% yield) according to similar steps in embodiment 1 by taking 2,5-dihydro-1H-pyrrole-3-(tetrahydropyrane-2-oxo)-formamide (100 mg, 0.5 mmol) and 3,4-dimethoxybenzenesulfonyl chloride (114 mg, 0.6 mmol; manufacturer: J&K Scientific LTD.) as raw materials;

MS (ESI) m/z 329(M+1)⁺.
¹HNMR(400 Hz, DMSO-D₆) δ=10.80(s, 1H), 9.13(s, 1H), 7.50-7.48(m, 1H), 7.31-7.24(m, 2H), 6.38(s, 1H), 4.24 (s, 4H), 3.92(s, 3H).

Embodiment 18

Preparation of N-hydroxy-1-((4-(1,2,36-tetrahydropyridine-4-yl)phenyl)sulfonyl)2,5-dihydro-1H -pyrrole-3-formamide

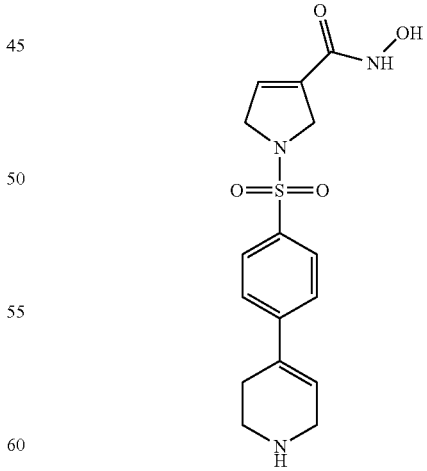

comprising the following step: preparing white solid N-hydroxy-1((4-(1,2,36-tetrahydropyridine-4-yl)phenyl)sulfonyl)2,5-dihydro-1H-pyrrole-3-formamide (26 mg, 15% yield) according to similar steps in embodiment 1 by taking 2,5-dihydro-1H-pyrrole-3-(tetrahydropyrane-2-oxo)-formamide (1000 mg, 0.5 mmol) and 4-(1,2,36-tetrahydropyridine-4-yl)phenyl) sulfonyl chloride (114 mg, 0.6 mmol; manufacturer: J&K Scientific LTD.) as raw materials:

MS (ESI) m/z 350(M+1)⁺.

Embodiment 19

Preparation of N-(2-aminophenyl)-1-(benzenesulfonyl)-2,5-dihydro-1H-pyrrole-3-formamide 1. Preparation of 2,5-dihydro-1H-pyrrole-3-ethyl formate

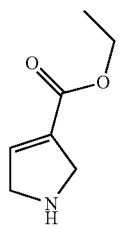

comprising the following steps: dissolving N-t-butyloxycarboryl-2,5-dihydro-1H-pyrrole-3-ethyl formate (250 mg, 1.1 mmol) in 5 mL of dichloromethane solution in an ice bath, dripping 2 mL of trifluoroacetic acid, stirring, slowly rising to the temperature of 25° C., and continuously stirring to react for 2 hours to obtain a reaction solution; and concentrating the reaction solution to obtain a yellow oily matter 2,5-dihydro-1H-pyrrole-3-ethyl formate (150 mg, 99% yield).

MS (EST) m/z 142(M+1)+.

2. Preparation of 1-phenyl sulfonyl-2,5-dihydro-1H-pyrrole-3-ethyl formate

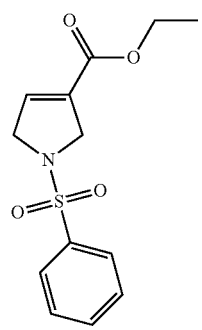 [SMILES: CCOC(=O)C1=CCN(S(=O)(=O)c2ccccc2)C1]

comprising the following steps: slowly adding benzene sulfonyl chloride (222 mg, 1.3 mmol) into a dichloromethane (10 mL) solution of 2,5-dihydro-1H-pyrrole-3-ethyl formate (150 mg, 1.1 mmol) and triethylamine (310 mg, 3.1 mmol) in an ice bath, slowly rising to the temperature of 25° C., and after continuously stirring to react for 2 hours, adding 10 mL of water to carry out a quenching reaction to obtain a reaction solution; extracting with ethyl acetate (50 mL×2), merging an organic phase, washing with a saturated salt solution (10 mL×2), and drying, filtering and concentrating the organic phase to obtain a crude product; and purifying the crude product through column chromatography (silica gel, a ratio of petroleum ether to ethyl acetate is 6:1), thereby obtaining a white solid compound 1-phenyl sulfonyl-2,5-dihydro-1H-pyrrole-3-ethyl formate (280 mg, 94% yield).

MS (ESI) m/z 281(M+1)⁺.

3. Preparation of 1-phenyl sulfonyl-2,5-dihydro-1H-pyrrole-3-formic acid

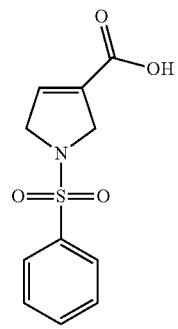 [SMILES: O=C(O)C1=CCN(S(=O)(=O)c2ccccc2)C1]

comprising the following steps: adding LiOH (179 mg, 4.5 mmol) into a solution of tetrahydrofuran (12 mL) and water (4 mL) of 1-phenyl sulfonyl-2,5-dihydro-1H-pyrrole-3-ethyl formate (280 mg, 1.0 mmol) at a temperature of 25° C. and stirring to stay overnight to obtain a reaction solution; then regulating the pH value of the reaction solution to 2 in an ice bath by using IN of hydrochloric acid, extracting with ethyl acetate (10 mL×3), and merging an organic phase; and drying, filtering and concentrating the organic phase, thereby obtaining 1-phenyl sulfonyl-2,5-dihydro-1H-pyrrole-3-formic acid (223 mg, 64% yield), wherein the obtained product does not need to be further purified and is directly used for the next reaction step.

MS (ESI) m/z 267(M+1)⁺.

4. Preparation of N-(2-aminophenyl)-1-(benzenesulfonyl)-2,5-dihydro-1H-pyrrole-3-formamide

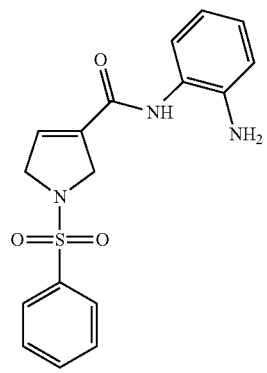 [SMILES: Nc1ccccc1NC(=O)C1=CCN(S(=O)(=O)c2ccccc2)C1]

comprising the following steps: dissolving 1-phenyl sulfonyl-2,5-dihydro-1H-pyrrole-3,formic acid (223 mg, 0.6 mmol) 10 mL of dichloromethane, sequentially adding 1,2-diaminobenzene (104 mg, 0.9 mmol), HATU (338 mg 0.9 mmol) and DIEA (229 mg, 1.8 mmol) into the solution, and stirring at a temperature of 25° C. to stay overnight to obtain a reaction solution; diluting the reaction solution with 20 mL of water, extracting with ethyl acetate (50 mL×2), and merging an organic phase; drying, filtering and concentrating the organic phase to obtain a crude product and purifying the crude product through preparative high performance liquid chromatography, thereby obtaining N-(2-aminophenyl)-1-(benzenesulfonyl)-2,5-dihydro-1H-pyrrole-3-formamide (52 mg, 22% yield).

MS (EST) m/z 344(M+1)$^+$.

$^1$HNMR(400 MHz, CD3OD). δ9.5(br s, 1H),7.9-7.8(m, 2H),7.7-7.6(m, 3H), 7.1-7.0(m, 4H), 6.7(s, 1H), 4.3(s, 4H).

In order to describe the beneficial effects of the present invention, the present invention provides the following test examples:

Test example 1 Detection of biological viability

HDAC inhibitory viabilities of the compounds in the present invention are detected in detection of substrate deacetylation.

A: Detection of enzyme viability of histone deacetylase 6 (#50076, BPS Bioscience):

Acetyl of HDAC 6 on a substrate is removed, so that the substrate is activated and can be affected by a subsequently added developing solution, and fluorophore is released. The size of a fluorescence signal reflects the viability of the HDAC 6. An IC50 detection method of the enzyme is disclosed in Chuping Xu, Elisabetta Soragni improved Histone Deacetylase Inhibitors as Therapeutics for the Neurdegenerative DiseaseEriedreich's Ataxia: A New Synthetic Route. A total reaction system (100 μL/well) contains 0.35 ng/μL of HDAC 6, 20 μM of substrate and compounds of different concentrations. The fluorescence signal is measured within 30 minutes after incubation at a temperature of 37° C., inhibitory effects of the compounds are determined from the obtained data and mapped with the compound concentrations to obtain a concentration response curve, and the IC50 value is fitted according to a four-parameter model.

B: Detection of enzyme viability of histone deacetylase 3 (#50003, BPS Bioscience):

Acetyl of HDAC 3 on a substrate is removed, so that the substrate is activated and can be affected by the developing solution, and fluorophore is released. The size of a fluorescence signal reflects the viability of the HDAC 3. An IC50 detection method of the enzyme is disclosed in Chuping Xu, Elisabetta Soraeni Improved Histone Deacetylase Inhibitors as Therapeutics for the Neurdegenerative DiseaseFriedreich's Ataxia: A New Synthetic Route. A total reaction system (100 μL/well) contains 0.16 ng/μL of HDAC 3, 10 μM of substrate and compounds of different concentrations. The fluorescence signal is detected at Ex/Em=360/460 on line, inhibitory effects of the compounds are determined from the obtained data and mapped with the compound concentrations to obtain a concentration response curve, and the IC50 value is fitted according to a four-parameter model.

The compounds 1-19 prepared in the embodiments are subjected to detection of enzyme viability of histone deacetylase 6 (i.e., HDAC6) according to the method above. Test results are shown in Table 2, wherein the measured IC50 values of the compounds are classified as specified, as shown in Table 2:

"+" indicates that the measured IC50 of HDAC6 is more than 500 nM;

"++" indicates that the IC50 of HDAC6 is less than 300 nM and more than 100 nM;

"+++" indicates that the IC50 of HDAC6 is less than 100 nM.

The compounds 1-19 prepared in the embodiments are subjected to detection of enzyme viability of histone deacetylase 3 (i.e., HDAC3) according to the method above. Test results are shown in Table 2, wherein the measured IC50 values of the compounds are classified as specified, as shown in Table 2:

"+" indicates that the measured IC50 of HDAC3 is more than 1000 nM;

"++" indicates that the IC50 of HDAC3 is mare than 100 nM and less than 1000 nM;

"+++" indicates that the IC50 of HDAC3 is less than 100 nM.

TABLE 2

Inhibitory Viabilities of Compounds an HDAC6 & HDAC3

| Compound | Viability (HDAC6) | Viability (HDAC3) |
|---|---|---|
| 1 | ++ | N.D. |
| 2 | +++ | + |
| 3 | ++ | ++ |
| 4 | +++ | ++ |
| 5 | +++ | + |
| 6 | +++ | ++ |
| 7 | +++ | N.D. |
| 8 | +++ | ++ |
| 9 | +++ | N.D. |
| 10 | +++ | N.D. |
| 11 | +++ | N.D. |
| 12 | +++ | N.D. |
| 13 | +++ | N.D. |
| 14 | +++ | N.D. |
| 15 | +++ | N.D. |
| 16 | +++ | N.D. |
| 17 | ++ | N.D. |
| 18 | ++ | N.D. |
| 19 | + | N.D. |

ND: data is in detection and analysis.

The tests indicate that the compounds 1-19 in the present invention have excellent histone deacetylase inhibitory viabilities and can be effectively used for treating diseases related to abnormal histone deacetylase viability.

Test example 2 Cell determination-determination of cell growth inhibition

Materials and reagents HepG2 cell strains, Hep3B cell strains, Huh7 cell strains and Li7 cell strains are purchased from Shanghai Institutes for Biological Sciences of Chinese Academy of Sciences; DMEM high glucose media and MEM media are purchased from Hyclone; fetal calf serum is purchased from Gibco Company; trypsin is purchased from Invitrogen Shanghai; CCK-8 kits are purchased from Beyotime Institute of Biotechnology; and other consumables such as cell-culture dishes and the like are purchased from Corning China.

Cell preparation before compound effect comprising the steps: digesting HepG2 cells, Hep3B Huh7 cells and Li7 cells in logarithmic phases by using the trypsin; after counting the cells by taking uniform cell suspension, adjusting cell density to 1500 cells/pore by using a culture medium containing 10% of serum, and re-inoculating into a 96-pore cell culture plate, wherein the culture volume is 200 μL; incubating in a 5% $CO_2$ incubator at a temperature of 37° C.; and culturing for 24 hours for experiments.

Compound effect comprising the steps: taking the cells cultured for 24 hours from the incubator, sucking culture solution in the pore plate, adding 200 μL of compound solution prepared by using a culture medium containing 10% of the fetal calf serum into each pore, enabling five pores of each concentration to be parallel, setting DMSO at negative control, and incubating in the 5% CO$_2$ incubator at a temperature of 37° C. for 72 hours for performing CCK-8 detection.

CCK-8 detection comprising the steps: taking a serum-free medium and a CCK-8 solution, and preparing a CCK-8 working solution according to a ratio of 10:1 (the process needs to be protected from light);

taking the cells cultured for 72 hours from the incubator, sucking culture solution in the pore plate, adding 120 μL of the CCK-8 working solution into each pore, adding 120 μL of the CCK-8 working solution into a cell-free pore plate to serve as blank control, and incubating in the 5% CO$_2$ incubator at a temperature of 37° C. for one hour (the process needs to be protected from light ); and taking the pore plate from the incubator, sucking 100 μL of solution from each pore into a new 96-pore plate, and reading absorbancy at 450 nm (the process needs to be protected from light).

Data processing:

$$\% \text{ Cell Viability} = \frac{100 \times (Tx - B)}{C - B}$$

Tx: absorbancy measured in CCK-8 within 72 hours after compound effect

C: absorbancy measured m CCK-8 within 72 hours after culturing in negative control pores B: absorbancy measured CCK-8 in blank control pores The compounds 1-19 prepared in the embodiments are operated in the above determination, and test results are shown in Table 3, wherein the highest measured IC50 values of the various compounds during single or multiple operations are classified as specified, as shown in Table 3:

"+" indicates that the measured IC50 values of the compounds in cancer cells are more than 10 uM;

"++" indicates that the measured IC50 values of the compounds in the cancer cells are less than 10 uM;

TABLE 3

Inhibitory Viabilities of Compounds on Different Hepatoma Cells

| Compound | HepG2 | Huh-7 | Li-7 | Hep3B |
|---|---|---|---|---|
| 1 | + | + | + | + |
| 2 | + | + | + | + |
| 3 | + | + | + | + |
| 4 | + | + | + | + |
| 5 | + | + | + | + |
| 6 | + | + | + | + |
| 7 | + | + | + | + |
| 8 | + | + | + | + |
| 9 | + | + | + | + |
| 10 | + | + | + | + |
| 11 | + | + | + | + |
| 12 | ++ | + | + | + |
| 13 | ++ | + | ++ | ++ |
| 14 | ++ | + | ++ | ++ |
| 15 | ++ | + | ++ | ++ |
| 16 | ++ | + | + | + |
| 17 | + | + | + | + |
| 18 | + | + | + | + |
| 19 | + | + | + | + |

The tests indicate that the compounds 1-19 in the present invention have excellent inhibitory viabilities on different hepatoma carcinoma cells (HepG2, Huh-7, Li-7 and Hep3B).

In conclusion, the novel compound shown as the formula I disclosed in the present invention shows good histone deacetylase inhibitory viability, and a novel medicinal possibility is provided for clinically treating diseases related to abnormal histone deacetylase viability. Meanwhile, a method for preparing the novel compound in the present invention has the advantages of fewer steps, simple and convenient operation, safety, environment friendliness, high yield and the like and is very suitable for industrial application.

What is claimed is:

1. A pyrrolic amide compound of formula I, or a pharmaceutically acceptable salt thereof:

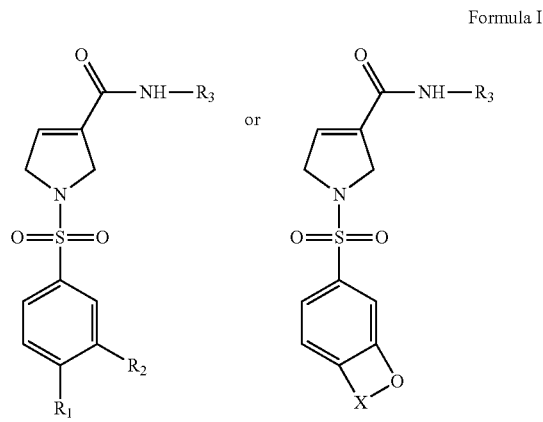

Formula I wherein

R$_1$ is selected from hydrogen, hydroxyl, cyano, halogen, carboxyl, C$_1$ -C$_6$ alkyl, C$_1$ -C$_6$ alkoxy, C$_2$ -C$_6$ acylamino, C$_2$ -C$_6$ aminoacyl, C$_3$ -C$_6$ heterocyclic radical, C$_3$-C$_6$ heterocyclic alkenyl or phenoxy;

R$_2$ is selected from hydrogen, hydroxyl, cyano, halogen, carboxyl, C$_1$ -C$_6$ alkyl, C$_1$ -C$_6$ alkoxy, C$_2$ -C$_6$ acylamino, C$_2$ -C$_6$ aminoacyl, C$_3$ -C$_6$ heterocyclic radical, C$_3$ -C$_6$ heterocyclic alkenyl, phenoxy, phenyl or substituted phenyl;

R$_3$ is selected from hydroxyl, amino-substituted phenyl, thiol or epoxy ketone groups;

X is selected from

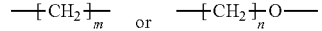

group, m is 0, 1, 2 or 3, and n is 0, 1 or 2.

2. The pyrrolic amide compound of claim 1, or a pharmaceutically acceptable salt thereof, wherein R₁ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamido, n-butyramido, isobutyramido, tert-butyramido, pentaneamide, hexaneamide, methylaminoacyl, ethylaminoacyl, n-propylaminoacyl, isopropylaminoacyl, n-butylaminoacyl, isobutylaminoacyl, tert-butylaminoacyl, pentylaminoacyl, hexylaminoacyl, C₃ N-heterocyclic radical, C₄ N-heterocyclic radical, C₅ N-heterocyclic radical, C₆ N-heterocyclic radical, C₃ N-heterocyclic alkenyl, C₄ N-heterocyclic alkenyl, C₅ N-heterocyclic alkenyl, C₆ N-heterocyclic alkenyl or phenoxy;

R₂ is selected from hydrogen, hydroxyl, cyano, fluorine, chlorine, bromine, carboxyl, methyl, ethyl, n-propyl, isopropyl, n-butyl, isobutyl, tert-butyl, pentyl, hexyl, methoxy, ethoxy, n-propoxy, isopropoxy, n-butoxy, isobutoxy, tert-butoxy, pentalkoxy, hexalkoxy, formamido, acetamido, n-propionamido, isopropylamide, n-butyramido, isobutyramido, tert-butyramido, pentaneamide, hexaneamide, methylaminoacyl, Ethylaminoacyl, n-propylaminoacyl, isopropylaminoacyl, n-butylaminoacyl, isobutylaminoacyl, tert-butylaminoacyl, pentylaminoacyl, hexylaminoacyl, C₃ N-heterocyclic radical, C₄ N-heterocyclic radical, C₅ N-heterocyclic radical, C₆ N-heterocyclic radical, C₃ N-heterocyclic alkenyl, C₄ N-heterocyclic alkenyl, C₅ N-heterocyclic alkenyl, C₆ N-heterocyclic alkenyl, phenoxy, phenyl or substituted phenyl;

R₁ and R₂ are not simultaneously hydrogen;

R₃ is selected from hydroxyl, amino-substituted phenyl or thiol; and m is 1 or 2, and n is 1 or 2.

3. The pyrrolic amide compound of claim 1, or a pharmaceutically acceptable salt thereof, wherein the pyrrolic amide compound of formula I is:

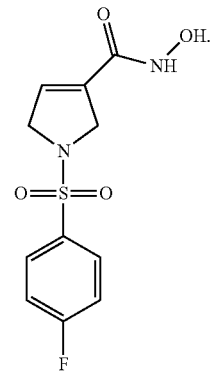

4. A pharmaceutical composition for inhibiting the histone deacetylase activity, comprising the pyrrolic amide compound of claim 1 or a pharmaceutically acceptable salt thereof as an active ingredient and an excipient or auxiliary.

5. The pharmaceutical composition of claim 4, wherein the pharmaceutical composition comprises an oral administration preparation, a sublingual administration preparation, a buccal administration preparation, a transdermal absorption preparation or an injection preparation.

* * * * *